(12) United States Patent
Harkins et al.

(10) Patent No.: US 6,682,902 B2
(45) Date of Patent: Jan. 27, 2004

(54) DNA ENCODING A NOVEL RG1 POLYPEPTIDE

(75) Inventors: Richard Harkins, Alameda, CA (US); Deborah Parkes, Hayward, CA (US); Gordon Parry, Walnut Creek, CA (US); Douglas W. Schneider, Lafayette, CA (US); Renate Steinbrecher, Walnut Creek, CA (US)

(73) Assignee: Schering Aktiengesellschaft, Berlin (DE)

( * ) Notice: Subject to any disclaimer, the term of this patent is extended or adjusted under 35 U.S.C. 154(b) by 244 days.

(21) Appl. No.: 09/732,357

(22) Filed: Dec. 7, 2000

(65) Prior Publication Data

US 2002/0004047 A1 Jan. 10, 2002

Related U.S. Application Data

(60) Provisional application No. 60/172,370, filed on Dec. 16, 1999.

(51) Int. Cl.$^7$ ............................................... G01N 33/53
(52) U.S. Cl. ...................................... 435/7.23; 424/9.1
(58) Field of Search ........................... 435/7.23; 424/9.1

(56) References Cited

U.S. PATENT DOCUMENTS

| | | |
|---|---|---|
| 5,804,382 A | 9/1998 | Sytkowski et al. |
| 5,871,969 A | 2/1999 | Hastings et al. |

FOREIGN PATENT DOCUMENTS

| | | |
|---|---|---|
| WO | WO98/45442 | 10/1998 |
| WO | WO98/50073 | 11/1998 |
| WO | WO99/46281 | 9/1999 |
| WO | WO00/23108 | 4/2000 |

OTHER PUBLICATIONS

Mikayama et al. (PNAS, 1993. 90: 10056–10060).*
Ngo et al, in The Protein Folding Problem and Tertiary Structure Prediction, 1994. (ed.), Birkhauser, Boston, MA, pp. 433 and 492–495.*
Kulvinder et al. (Biochem. Cell Biol. 1991; 69: 415–417).*
(The Journal of Biological Chemistry 1989; 264(35): 20823–20826).*
Higashijima et al., "Mindin/F–Spondin Family: Novel ECM Proteins Expressed in the Zebrafish Embryonic Axis" *Developmental Biology* (1997) 192:211–227.
Umemiya et al., "M–Spondin, a novel ECM protein highly homologous to vertebrate F–spondin, is localized at the muscle attachment sites in the Drosophila embryo", *Develop. Biol.* (1997) 186:165–176.
Manda et al., "Identification of genes (SPON2 and C20orf2) differentially expressed between cancerous and noncancerous lung cells by mRNA differential display", *Genomics*(1999) 61:5–14.
Klar et al., "F–spondin: a gene expressed at high levels in the floor plate encodes a secreted protein that promotes neural cell adhesionand neurite extension", *Cell*(1992) 69:95–110.
Feinstein et al., "F–spondin and mindin: two structually and functionally related genes expressed in the hippocampus that promote outgrowth of embryonic hippocampal neurons" *Development* (1999) 126:3637–3648.
Burstyn–Cohen et al., "Accumulation of F–spondin in injured peripheral nerve promotes the outgrowth of sensory axons", *J. Neuroscience* (1998)18(21):8875–8885.
Sodeem et al., "Preliminary Imaging Results Using In–11 Labeled CYT–356 (Prostascint™) in the Detection of Recurrent Prostate Cancer" *Clinical Nuclear Medicine* (1996)21:759–767.

* cited by examiner

*Primary Examiner*—Patrick J. Nolan
(74) *Attorney, Agent, or Firm*—Wendy L. Washtien

(57) ABSTRACT

The present invention relates to novel human extracellular matrix polypeptides, designated RG1, polynucleotides encoding the polypeptides, methods for producing the polypeptides, expression vectors and genetically engineered host cells for expression of the polypeptides. The invention further relates to methods for utilizing the polynucleotides and polypeptides in research, diagnosis, and therapeutic applications.

11 Claims, 10 Drawing Sheets

FIGURE 1

```
   1  AGAAAGGGGT GCGGCAGCAC TGCCAGGGGA AGAGGGTGAT CCGACCCGGG
  51  GAAGGTCGCT GGGCAGGGCG AGTTGGGAAA GCGGCAGCCC CGCCGCCCC
 101  CGCAGCCCCT TCTCCTCCTT TCTCCCACGT CCTATCTGCC TCTCGCTGGA
 151  GGCCAGGCCG TGCAGCATCG AAGACAGGAG GAACTGGAGC CTCATTGGCC
 201  GGCCCGGGGC GCCGGCCTCG GCTTAAATA GGAGCTCCGG GCTCTGGCTG
 251  GGACCCGACC GCTGCCGGCC GCGCTCCCGC TGCTCCTGCC GGGTGATGGA
 301  AAACCCCAGC CCGGCCGCCG CCCTGGGCAA GGCCCTCTGC GCTCTCCTCC
 351  TGGCCACTCT CGGCGCCGCC GGCCAGCCTC TTGGGGGAGA GTCCATCTGT
 401  TCCGCCGGAG CCCCGGCCAA ATACAGCATC ACCTTCACGG GCAAGTGGAG
 451  CCAGACGGCC TTCCCCAAGC AGTACCCCCT GTTCCGCCCC CCTGCGCAGT
 501  GGTCTTCGCT GCTGGGGGCC GCGCATAGCT CCGACTACAG CATGTGGAGG
 551  AAGAACCAGT ACGTCAGTAA CGGGCTGCGC GACTTTGCGG AGCGCGGCGA
 601  GGCCTGGGCG CTGATGAAGG AGATCGAGGC GGCGGGGGAG GCGCTGCAGA
 651  GCGTGCACGC GGTGTTTTCG GCGCCCGCCG TCCCCAGCGG CACCGGGCAG
 701  ACGTCGGCGG AGCTGGAGGT GCAGCGCAGG CACTCGCTGG TCTCGTTTGT
 751  GGTGCGCATC GTGCCCAGCC CCGACTGGTT CGTGGGCGTG GACAGCCTGG
 801  ACCTGTGCGA CGGGGACCGT TGGCGGGAAC AGGCGGCGCT GGACCTGTAC
 851  CCCTACGACG CCGGGACGGA CAGCGGCTTC ACCTTCTCCT CCCCCAACTT
 901  CGCCACCATC CCGCAGGACA CGGTGACCGA GATAACGTCC TCCTCTCCCA
 951  GCCACCCGGC CAACTCCTTC TACTACCCAC GGCTGAAGGC CCTGCCTCCC
1001  ATCGCCAGGG TGACACTGGT GCGGCTGCGA CAGAGCCCCA GGGCCTTCAT
1051  CCCTCCCGCC CCAGTCCTGC CCAGCAGGGA CAATGAGATT GTAGACAGCG
1101  CCTCAGTTCC AGAAACGCCG CTGGACTGCG AGGTCTCCCT GTGGTCGTCC
```

FIGURE 1 – continued

```
1151  TGGGGACTGT GCGGAGGCCA CTGTGGGAGG CTCGGGACCA AGAGCAGGAC
1201  TCGCTACGTC CGGGTCCAGC CCGCCAACAA CGGGAGCCCC TGCCCCGAGC
1251  TCGAAGAAGA GGCTGAGTGC GTCCCTGATA ACTGCGTCTA AGACCAGAGC
1301  CCCGCAGCCC CTGGGCCCC CCGGAGCCAT GGGGTGTCGG GGGCTCCTGT
1351  GCAGGCTCAT GCTGCAGGCG GCCGAGGGCA CAGGGGGTTT CGCGCTGCTC
1401  CTGACCGCGG TGAGGCCGCG CCGACCATCT CTGCACTGAA GGGCCCTCTG
1451  GTGGCCGGCA CGGGCATTGG GAAACAGCCT CCTCCTTTCC CAACCTTGCT
1501  TCTTAGGGGC CCCCGTGTCC CGTCTGCTCT CAGCCTCCTC CTCCTGCAGG
1551  ATAAAGTCAT CCCCAAGGCT CCAGCTACTC TAAATTATGT CTCCTTATAA
1601  GTTATTGCTG CTCCAGGAGA TTGTCCTTCA TCGTCCAGGG GCCTGGCTCC
1651  CACGTGGTTG CAGATACCTC AGACCTGGTG CTCTAGGCTG TGCTGAGCCC
1701  ACTCTCCCGA GGGCGCATCC AAGCGGGGC CACTTGAGAA GTGAATAAAT
1751  GGGGCGGTTT CGGAAGCGTC
```

FIGURE 2

```
  1  MENPSPAAAL GKALCALLLA TLGAAGQPLG GESICSAGAP AKYSITFTGK
 51  WSQTAFPKQY PLFRPPAQWS SLLGAAHSSD YSMWRKNQYV SNGLRDFAER
101  GEAWALMKEI EAAGEALQSV HAVFSAPAVP SGTGQTSAEL EVQRRHSLVS
151  FVVRIVPSPD WFVGVDSLDL CDGDRWREQA ALDLYPYDAG TDSGFTFSSP
201  NFATIPQDTV TEITSSSPSH PANSFYYPRL KALPPIARVT LVRLRQSPRA
251  FIPPAPVLPS RDNEIVDSAS VPETPLDCEV SLWSSWGLCG GHCGRLGTKS
301  RTRYVRVQPA NNGSPCPELE EEAECVPDNC V
```

FIGURE 3

```
RG1     1 MENPSPAAALGKALCALLLATLGA.AGQPLGGESICSAGAPAKYSITFTG  49
          ||| |  .| : |   ||| ||. ||||||||:|.|   |:|||||||
mindin  1 MENVS..FSLDRTLWVFLLAMLGSTAGQPLGGESVCTARPLARYSITFTG  48

50 KWSQTAFPKQYPLFRPPAQWSSLLGAAHSSDYSMWRKNQYVSNGLRDFAE  99
          |||||||||||||||||||||||||||||||||||||:||||||||||
       49 KWSQTAFPKQYPLFRPPAQWSSLLGAAHSSDYSMWRKNEYVSNGLRDFAE  98

100 RGEAWALMKEIEAAGEALQSVHAVFSAPAVPSGTGQTSAELEVQRRHSLV 149
          ||||||||||||||| |||||||||||||||||||||||||| |||||
       99 RGEAWALMKEIEAAGEKLQSVHAVFSAPAVPSGTGQTSAELEVHPRHSLV 148

150 SFVVRIVPSPDWFVGVDSLDLCDGDRWREQAALDLYPYDAGTDSGFTFSS 199
          |||||||||||||:||||||:||:||  |||||:||||||||||||||
      149 SFVVRIVPSPDWFVGIDSLDLCEGGRWKEQVVLDLYPHDAGTDSGFTFSS 198

200 PNFATIPQDTVTEITSSSPSHPANSFYYPRLKALPPIARVTLVRLRQSPR 249
          |||||||||||||.||||||||||||||.|||||:|| ||||||||
      199 PNFATIPQDTVTEITASSPSHPANSFYYPRLKSLPPIAKVTFVRLRQSPR 248

250 AFIPPAPVLPSRDNEIVDSASVPETPLDCEVSLWSSWGLCGGHCGRLGTK 299
          || ||.  | ||  |||||  |||||||||||||||||||||:|| | |
      249 AFAPPSLDLASRGNEIVDSLSVPETPLDCEVSLWSSWGLCGGPCGKLGAK 298

300 SRTRYVVRVQPANNGSPCPELEEEAECVPDNCV 331
          |||||||||||||.||||||||||| ||||
      299 SRTRYVRVQPANNGTPCPELEEEAECAPDNCV 330
```

FIGURE 4

```
     AGAAAGGGGTGCGGCAGCACTGCCAGGGGAAGAGGGTGATCCGACCCGGGGAAGGTCGCT
  1  ------------+---------+---------+---------+---------+---------+ 60
     TCTTTCCCCACGCCGTCGTGACGGTCCCCTTCTCCCACTAGGCTGGGCCCCTTCCAGCGA

GGGCAGGGCGAGTTGGGAAAGCGGCAGCCCCGCCGCCCCGCAGCCCCTTCTCCTCCTT
 61  ------------+---------+---------+---------+---------+---------+ 120
     CCCGTCCCGCTCAACCCTTTCGCCGTCGGGGGCGGCGGGGGCGTCGGGGAAGAGGAGGAA

TCTCCCACGTCCTATCTGCCTCTCGCTGGAGGCCAGGCCGTGCAGCATCGAAGACAGGAG
 121 ------------+---------+---------+---------+---------+---------+ 180
     AGAGGGTGCAGGATAGACGGAGAGCGACCTCCGGTCCGGCACGTCGTAGCTTCTGTCCTC

GAACTGGAGCCTCATTGGCCGGCCCGGGGCGCCGGCCTCGGGCTTAAATAGGAGCTCCGG
 181 ------------+---------+---------+---------+---------+---------+ 240
     CTTGACCTCGGAGTAACCGGCCGGGCCCCGCGGCCGGAGCCCGAATTTATCCTCGAGGCC

GCTCTGGCTGGGACCCGACCGCTGCCGGCCGCGCTCCCGCTGCTCCTGCCGGGTGATGGA
 241 ------------+---------+---------+---------+---------+---------+ 300
     CGAGACCGACCCTGGGCTGGCGACGGCCGGCGCGAGGGCGACGAGGACGGCCCACTACCT b                                                            M  E  -

AAACCCCAGCCCGGCCGCCGCCCTGGGCAAGGCCCTCTGCGCTCTCCTCCTGGCCACTCT
 301 ------------+---------+---------+---------+---------+---------+ 360
     TTTGGGGTCGGGCCGGCGGCGGGACCCGTTCCGGGAGACGCGAGAGGAGGACCGGTGAGA b        N  P  S  P  A  A  A  L  G  K  A  L  C  A  L  L  L  A  T  L  -

CGGCGCCGCCGGCCAGCCTCTTGGGGGAGAGTCCATCTGTTCCGCCGGAGCCCCGGCCAA
 361 ------------+---------+---------+---------+---------+---------+ 420
     GCCGCGGCGGCCGGTCGGAGAACCCCCTCTCAGGTAGACAAGGCGGCCTCGGGGCCGGTT b        G  A  A  G  Q  P  L  G  G  E  S  I  C  S  A  G  A  P  A  K  -

ATACAGCATCACCTTCACGGGCAAGTGGAGCCAGACGGCCTTCCCCAAGCAGTACCCCCT
 421 ------------+---------+---------+---------+---------+---------+ 480
     TATGTCGTAGTGGAAGTGCCCGTTCACCTCGGTCTGCCGGAAGGGGTTCGTCATGGGGA b        Y  S  I  T  F  T  G  K  W  S  Q  T  A  F  P  K  Q  Y  P  L  -

GTTCCGCCCCCCTGCGCAGTGGTCTTCGCTGCTGGGGGCCGCGCATAGCTCCGACTACAG
 481 ------------+---------+---------+---------+---------+---------+ 540
     CAAGGCGGGGGGACGCGTCACCAGAAGCGACGACCCCCGGCGCGTATCGAGGCTGATGTC b        F  R  P  P  A  Q  W  S  S  L  L  G  A  A  H  S  S  D  Y  S  -

CATGTGGAGGAAGAACCAGTACGTCAGTAACGGGCTGCGCGACTTTGCGGAGCGCGGCGA
 541 ------------+---------+---------+---------+---------+---------+ 600
     GTACACCTCCTTCTTGGTCATGCAGTCATTGCCCGACGCGCTGAAACGCCTCGCGCCGCT b        M  W  R  K  N  Q  Y  V  S  N  G  L  R  D  F  A  E  R  G  E  -
```

FIGURE 4 - continued

```
      GGCCTGGGCGCTGATGAAGGAGATCGAGGCGGCGGGGGAGGCGCTGCAGAGCGTGCACGC
601   ---------+---------+---------+---------+---------+---------+ 660
      CCGGACCCGCGACTACTTCCTCTAGCTCCGCCGCCCCCTCCGCGACGTCTCGCACGTGCG b       A   W   A   L   M   K   E   I   E   A   A   G   E   A   L   Q   S   V   H   A   -

GGTGTTTTCGGCGCCCGCCGTCCCCAGCGGCACCGGGCAGACGTCGGCGGAGCTGGAGGT
661   ---------+---------+---------+---------+---------+---------+ 720
      CCACAAAAGCCGCGGGCGGCAGGGGTCGCCGTGGCCCGTCTGCAGCCGCCTCGACCTCCA b       V   F   S   A   P   A   V   P   S   G   T   G   Q   T   S   A   E   L   E   V   -

GCAGCGCAGGCACTCGCTGGTCTCGTTTGTGGTGCGCATCGTGCCCAGCCCCGACTGGTT
721   ---------+---------+---------+---------+---------+---------+ 780
      CGTCGCGTCCGTGAGCGACCAGAGCAAACACCACGCGTAGCACGGGTCGGGGCTGACCAA b       Q   R   R   H   S   L   V   S   F   V   V   R   I   V   P   S   D   W   F   -

CGTGGGCGTGGACAGCCTGGACCTGTGCGACGGGGACCGTTGGCGGGAACAGGCGGCGCT
781   ---------+---------+---------+---------+---------+---------+ 840
      GCACCCGCACCTGTCGGACCTGGACACGCTGCCCCTGGCAACCGCCCTTGTCCGCCGCGA b       V   G   V   D   S   L   D   L   C   D   G   D   R   W   R   E   Q   A   A   L   -

GGACCTGTACCCCTACGACGCCGGGACGGACAGCGGCTTCACCTTCTCCTCCCCCAACTT
841   ---------+---------+---------+---------+---------+---------+ 900
      CCTGGACATGGGGATGCTGCGGCCCTGCCTGTCGCCGAAGTGGAAGAGGAGGGGGTTGAA b       D   L   Y   P   Y   D   A   G   T   D   S   G   F   T   F   S   S   P   N   F   -

CGCCACCATCCCGCAGGACACGGTGACCGAGATAACGTCCTCCTCTCCCAGCCACCCGGC
901   ---------+---------+---------+---------+---------+---------+ 960
      GCGGTGGTAGGGCGTCCTGTGCCACTGGCTCTATTGCAGGAGGAGAGGGTCGGTGGGCCG b       A   T   I   P   Q   D   T   V   T   E   I   T   S   S   S   P   S   H   P   A   -

CAACTCCTTCTACTACCCACGGCTGAAGGCCCTGCCTCCCATCGCCAGGGTGACACTGGT
961   ---------+---------+---------+---------+---------+---------+ 1020
      GTTGAGGAAGATGATGGGTGCCGACTTCCGGGACGGAGGGTAGCGGTCCCACTGTGACCA b       N   S   F   Y   Y   P   R   L   K   A   L   P   P   I   A   R   V   T   L   V   -

GCGGCTGCGACAGAGCCCCAGGGCCTTCATCCCTCCCGCCCCAGTCCTGCCCAGCAGGGA
1021  ---------+---------+---------+---------+---------+---------+ 1080
      CGCCGACGCTGTCTCGGGGTCCCGGAAGTAGGGAGGGCGGGGTCAGGACGGGTCGTCCCT b       R   L   R   Q   S   P   R   A   F   I   P   P   A   P   V   L   P   S   R   D   -

CAATGAGATTGTAGACAGCGCCTCAGTTCCAGAAACGCCGCTGGACTGCGAGGTCTCCCT
1081  ---------+---------+---------+---------+---------+---------+ 1140
      GTTACTCTAACATCTGTCGCGGAGTCAAGGTCTTTGCGGCGACCTGACGCTCCAGAGGGA b       N   E   I   V   D   S   A   S   V   P   E   T   P   L   D   C   E   V   S   L   -
```

FIGURE 4 - continued

```
        GTGGTCGTCCTGGGGACTGTGCGGAGGCCACTGTGGGAGGCTCGGGACCAAGAGCAGGAC
1141    ---------+---------+---------+---------+---------+---------+  1200
        CACCAGCAGGACCCCTGACACGCCTCCGGTGACACCCTCCGAGCCCTGGTTCTCGTCCTG b         W   S   S   W   G   L   C   G   G   H   C   G   R   L   G   T   K   S   R   T   -

TCGCTACGTCCGGGTCCAGCCCGCCAACAACGGGAGCCCCTGCCCCGAGCTCGAAGAAGA
1201    ---------+---------+---------+---------+---------+---------+  1260
        AGCGATGCAGGCCCAGGTCGGGCGGTTGTTGCCCTCGGGGACGGGGCTCGAGCTTCTTCT b         R   Y   V   R   V   Q   P   A   N   N   G   S   P   C   P   E   L   E   E   E   -

GGCTGAGTGCGTCCCTGATAACTGCGTCTAAGACCAGAGCCCCGCAGCCCCTGGGGCCCC
1261    ---------+---------+---------+---------+---------+---------+  1320
        CCGACTCACGCAGGGACTATTGACGCAGATTCTGGTCTCGGGGCGTCGGGGACCCCGGGG b         A   E   C   V   P   D   N   C   V   *                                           -

CCGGAGCCATGGGGTGTCGGGGGCTCCTGTGCAGGCTCATGCTGCAGGCGGCCGAGGGCA
1321    ---------+---------+---------+---------+---------+---------+  1380
        GGCCTCGGTACCCCACAGCCCCCGAGGACACGTCCGAGTACGACGTCCGCCGGCTCCCGT

CAGGGGGTTTCGCGCTGCTCCTGACCGCGGTGAGGCCGCGCCGACCATCTCTGCACTGAA
1381    ---------+---------+---------+---------+---------+---------+  1440
        GTCCCCCAAAGCGCGACGAGGACTGGCGCCACTCCGGCGCGGCTGGTAGAGACGTGACTT

GGGCCCTCTGGTGGCCGGCACGGGCATTGGGAAACAGCCTCCTCCTTTCCCAACCTTGCT
1441    ---------+---------+---------+---------+---------+---------+  1500
        CCCGGGAGACCACCGGCCGTGCCCGTAACCCTTTGTCGGAGGAGGAAAGGGTTGGAACGA

TCTTAGGGGCCCCCGTGTCCCGTCTGCTCTCAGCCTCCTCCTCCTGCAGGATAAAGTCAT
1501    ---------+---------+---------+---------+---------+---------+  1560
        AGAATCCCCGGGGGCACAGGGCAGACGAGAGTCGGAGGAGGAGGACGTCCTATTTCAGTA

CCCCAAGGCTCCAGCTACTCTAAATTATGTCTCCTTATAAGTTATTGCTGCTCCAGGAGA
1561    ---------+---------+---------+---------+---------+---------+  1620
        GGGGTTCCGAGGTCGATGAGATTTAATACAGAGGAATATTCAATAACGACGAGGTCCTCT

TTGTCCTTCATCGTCCAGGGGCCTGGCTCCCACGTGGTTGCAGATACCTCAGACCTGGTG
1621    ---------+---------+---------+---------+---------+---------+  1680
        AACAGGAAGTAGCAGGTCCCCGGACCGAGGGTGCACCAACGTCTATGGAGTCTGGACCAC

CTCTAGGCTGTGCTGAGCCCACTCTCCCGAGGGCGCATCCAAGCGGGGGCCACTTGAGAA
1681    ---------+---------+---------+---------+---------+---------+  1740
        GAGATCCGACACGACTCGGGTGAGAGGGCTCCCGCGTAGGTTCGCCCCCGGTGAACTCTT

GTGAATAAATGGGGCGGTTTCGGAAGCGTC
1741    ---------+---------+----------+  1770
        CACTTATTTACCCCGCCAAAGCCTTCGCAG
```

Expression of *Rg1* mRNA in human tissues

Purification of Native RG1 Protein Secreted by LNCaP Cells.

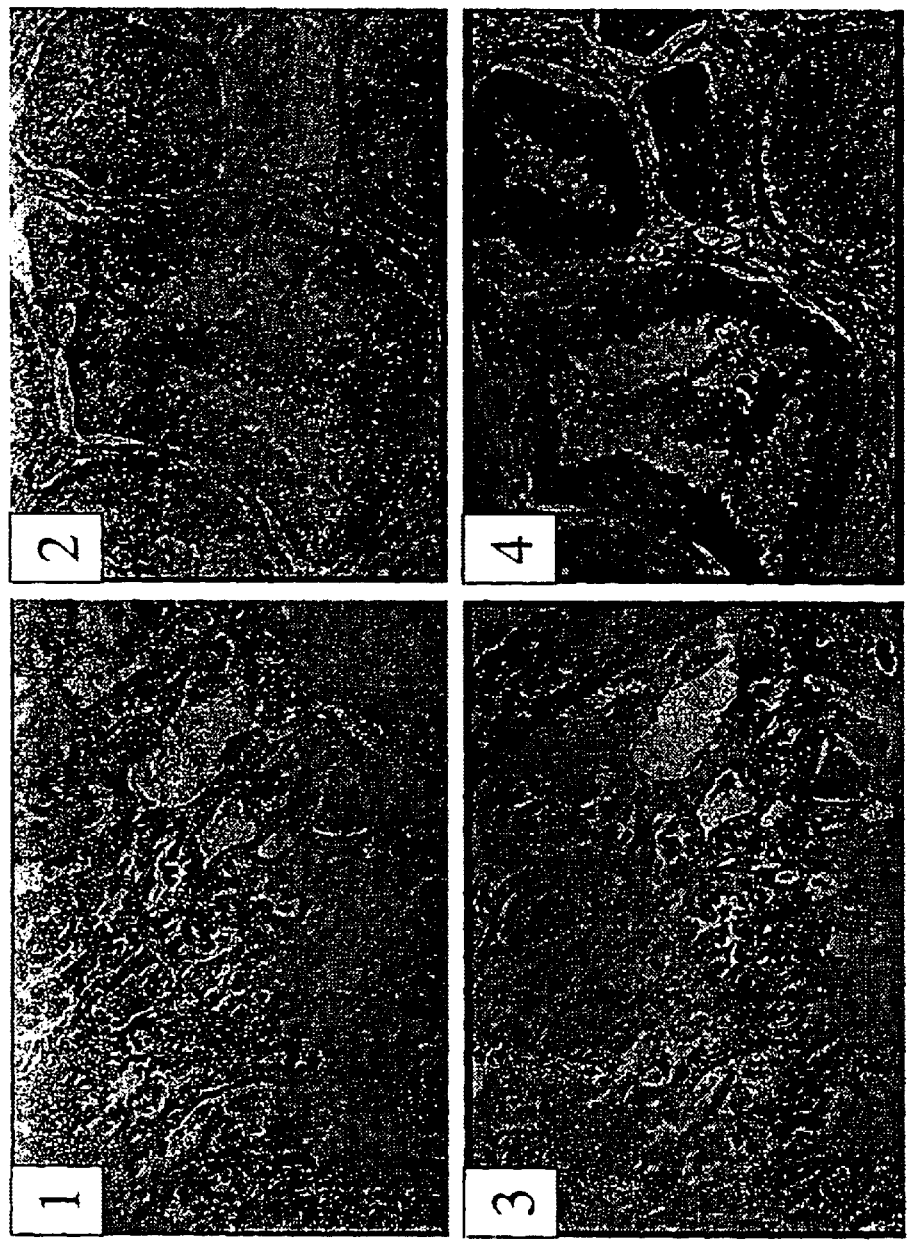
FIGURE 7: Immunohistochemical staining of RG1 expression
1(4x); 2 (40x) : prostate tissue, diluent negative control
3 (4x); 4 (40X): prostate tissue, anti Rg-1 antibody

DNA ENCODING A NOVEL RG1 POLYPEPTIDE

This application claims the benefit of U.S. Provisional Application No. 60/172,370, filed Dec. 16, 1999, which is incorporated herein in full by reference.

FIELD OF THE INVENTION

This invention relates, in part, to newly identified polynucleotides and polypeptides; variants and derivatives of the polynucleotides and polypeptides; methods of making the polynucleotides and polypeptides, and their variants and derivatives; antibodies directed toward the polypeptides, their variants and derivatives; and uses of the polynucleotides, polypeptides, variants, derivatives and antibodies. In particular, in these and in other regards, the invention relates to novel human extracellular matrix polypeptides (designated RG1), polynucleotides which encode these polypeptides, antibodies directed toward these polypeptides, and antisense polynucleotides that block RG1 expression.

BACKGROUND OF THE INVENTION

Prostate cancer is a frequently occurring disease in man, in that it is found in about one third of men over the age of 45. There is evidence for both genetic and environmental causes, with the majority of cases probably being the result of a combination of both factors. Studies of familial cancer have suggested that genetic predisposition plays a role in about 5–10% of all prostate cancers, and in about 45% of cases in men younger than 55.

There is evidence that prostate cancer develops as a multi-step disease, with one of the precursor lesions being prostatic intraepithelial neoplasia (PIN). Early stages of the disease are androgen dependent, while later stages are hormone independent. A proliferative disorder of the prostate known as benign prostatic hyperplasia is often detected clinically but is probably not a stage in the development of cancer. It is, however, frequently associated with prostate cancer. Cancers in the prostate are often multifocal, generally slow growing, and heterogeneous. Late stage cancers frequently metastasize to the lymph nodes and to the bone.

Prostate cancer is usually diagnosed by physical examination and by serum levels of prostate specific antigen (PSA). Radical prostatectomy is the treatment of choice for localized disease. Advanced metastatic disease is treated currently by androgen ablation induced by orchiectomy or treatment with GnRH (gonadotrophin releasing hormone), and by anti-androgen therapy. However, advanced disease almost invariably becomes hormone resistant and there is no cure for progressive disease. Moreover, there are serious side effects associated with both radical prostatectomy and androgen ablation therapy. These include a high risk of incontinence and impotence associated with radical prostatectomy and bone fractures and osteoporosis associated with androgen ablation therapy.

There is, therefore, a considerable need for new therapeutic approaches for both early and late stage prostate cancer. There is also a significant need for new diagnostic agents, in particular agents that can discriminate stages of the disease, as this significantly influences the treatment options. For example, if disease has progressed beyond the prostate and has metastasized to the lymph nodes, radical prostatectomy is not undertaken as it has no effect on progression, but may have significant unwanted side effects. An agent that could detect metastasis, in vivo, would have considerable value.

Changes in the expression of specific proteins have been demonstrated in prostate cancer including abnormal p53 expression in late stage prostate cancer, reduced levels of TGF-β receptors, reduced levels of E-cadherin, C-Cam (a cell adhesion molecule), and several integrins. The expression of the oncogene bcl-2 is strikingly elevated in late stage androgen independent tumors, and prognosis for patients expression bcl-2 at elevated levels is relatively poor. While the previously mentioned changes in gene expression are well documented, no changes in expression have been identified that have been demonstrated to be causative for the disease. It would, therefore, be useful to identify new proteins whose expression is linked to the presence or development of prostate tumors which could serve as molecular targets for prostate cancer diagnosis and therapy.

This invention discloses a new homologue to a superfamily of extracellular matrix proteins. This homologue, named RG1 is expressed in prostate tissue and may be overexpressed in prostate tumors.

The extracellular matrix is a complex meshwork of collagen and elastin, embedded in a viscoelastic ground substance composed of proteoglycans and glycoproteins. The matrix exists as a three dimensional supporting scaffold that isolates tissue compartments, mediates cell attachment and determines tissue architecture (Bissel et al., *J. Theor. Biol.* 99:31–68, 1982; Carlson et al., *Proc. Natl. Acad. Sci. USA* 78:2403–2406, 1981). The matrix acts as a macromolecular filter (Hay, E. D., *Cell Biology of Extracellular Matrix*, New York, Plenum Press, 1982) and also influences cytodifferentiation, mitogenesis, and morphogenesis (Gospodarowiczs, D., *Cancer Res.* 38:4155–171, 1978). The biochemical interactions between normal cells and the matrix may be altered in neoplasia, and this may influence tumor proliferation. Tumor cells can interact with the matrix in different ways. First, tumor cells can attach to the matrix via specific plasma membrane receptors (Terranova et al., *Cancer Res.* 42:2265–2269, 1982). Second, degradation of the matrix is mediated by a cascade of enzymes that are contributed by the tumor cell and the host (Eisen et al., *Bioch. Biophys. Acta* 151:637–645, 1968). Third, in differentiated areas of the tumor, tumor cells may synthesize and accumulate matrix or induce the host cell to accumulate excessive matrix (Brownstein et al., *Cancer* 40: 2979–2986, 1977).

RG1 shows homology to a superfamily of extracellular matrix proteins, encoded by the Mindin/F-spondin genes. The gene family is united by two conserved spondin domains, FS1 and FS2, near the amino terminus and at least one thrombospondin type 1 repeat (TSR1) at the carboxy terminus (Shimeld, S. M., *Mol. Biol. Evol.* 15(9): 1218–1223, 1998). The TSR motif was originally found in the vertebrate extracellular matrix proteins (Bornstein, P., *J. Cell Biol.* 130:503–506, 1995) and has subsequently been found in several other extracellular matrix proteins. There are several lines of evidence that TSR's mediate cell adhesion and play a key role in tumorigenesis. For example, it has been demonstrated that proteolytic fragments of thrombospondin that contain the TSR's, and synthetic peptides having sequences corresponding to the TSR region of thrombospondin, promote tumor cell adhesion and metastasis (Prater et al., *J. Cell Biol.* 112:1031–1040, 1991; Tuszynski and Nicosia, *BioEssays* 18:71–76, 1996), have antiangiogenic activity (Tolsma et al., *J. Cell Biol.* 122:497–511, 1993) and inhibit platelet aggregation and melanoma metastasis (Tuszynski et al., *J. Cell Biol.* 116:209–217, 1992).

Currently, the members of this superfamily include a gene in *Caenorhabditis elegans,* a single gene in Drosophila and multiple genes in vertebrates. In *C. elegans,* the gene F10E7.4 encodes for five TSR's in addition to the FS1 and FS2 domains (Higashijima et.al., *Dev. Biol.* 192:211–227, 1997). In Drosophila, the family member termed M-spondin (mspo) contains the FS1 and FS2 domains and a single TSR (Umemiya et al., *Dev. Biol.* 186:165–176, 1997). The M-spondin gene encodes a secreted protein that is localized at the muscle attachment sites and seems to function as an extracellular matrix protein that supports muscle—apodeme attachment. The family members in vertebrates include genes isolated from zebrafish (Mindin1 and Mindin2, F-spondin1, and F-spondin2), rat F-spondin, Xenopus F-spondin and rat Mindin. Mindin1 and Mindin2 are closely related to each other and have a gene structure similar to that of Drosophila M-spondin. Both Mindin1 and Mindin2 genes encode for a single TSR in addition to the FS1 and FS2 domains (Higashijima et.al., *Dev. Biol.* 192:211–227, 1997). Zebrafish F-spondinl and F-spondin2, rat F-spondin (Klar et al., *Cell* 69:95–110, 1992) and Xenopus F-spondin (Altaba et al., *Proc. Natl. Acad. Sci. USA* 90:8268–8272) genes all have similar structures, encoding six copies of the TSR's in addition to the FS1 and FS2 domains. In vertebrates, the Mindin/F-spondin superfamily can be classified into two groups: those genes closely related to the original rat F-spondin and Mindin genes and those genes closely related to the Drosophila M-spondin gene. Both vertebrate Mindin and F-spondin genes code for proteins that are primarily expressed by the floor plate of the neural tube during embryonic development.

Recently, a single F-spondin related gene, AmphiF-spondin, has been isolated from amphioxus (Shimeld, S. M., *Mol. Biol. Evol.* 15(9): 1218–1223,1998). Based on molecular phylogenetics, AmphiF-spondin is closely related to a particular subgroup of vertebrate F-spondin genes that encode six TSR's. AmphiF-spondin encodes three TSR's and two fibronectin type III repeats, one of which has strong identity to a fibronectin type III repeat from Deleted in Colorectal Cancer (DCC). The expression of the protein is found through most of the central nervous system and is not confined to the midline as described for the vertebrate Mindin and F-spondin proteins.

These data suggest that extracellular matrix proteins, such as the novel RG1 protein, which is a homologue of the Mindin/F-spondin superfamily, would be good candidates for use in diagnosis of cancer and therapeutic intervention.

SUMMARY OF THE INVENTION

The present invention provides a polynucleotide sequence which uniquely encodes a novel protein designated herein as RG1. The RG1 polypeptide shows homology to the rat Mindin extracellular matrix protein. It contains a hydrophobic signal sequence at the N-terminus, two spondin domains (FS1 and FS2), and a thrombospondin type 1 repeat at its C-terminus. RG1 shows 89.7% similarity to rat Mindin. The polynucleotide sequence, designated herein as rg1, and described herein in FIG. 1 (SEQ ID NO. 1), encodes the amino acid sequence for RG1, which is shown in FIG. 2 (SEQ ID NO. 2).

Toward these ends, and others, it is an object of the present invention to provide polypeptides, inter alia, that have been identified as novel proteins with homology to the Mindin family of extracellular matrix proteins, as shown by comparison of the amino acid sequence set out in FIG. 2 (SEQ ID NO: 2) and known amino acid sequences of other extracellular matrix proteins.

It is a further object of the invention, moreover, to provide polynucleotides that encode such polypeptides, particularly polynucleotides that encode the polypeptide designated herein as RG1.

In accordance with this aspect of the invention there are provided isolated polynucleotides encoding RG1, including mRNAs, cDNAs, and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of polynucleotides that encode variants of the polypeptide designated herein as RG1.

In accordance with this aspect of the invention there are provided novel polypeptides of human origin referred to herein as RG1 as well as biologically, diagnostically or therapeutically useful fragments, variants and derivatives thereof, variants and derivatives of the fragments, and analogs of the foregoing.

Among the particularly preferred embodiments of this aspect of the invention are variants of RG1 encoded by naturally occurring allelic variants of the rg1 polynucleotide.

It is another object of the invention to provide a method of producing the aforementioned polypeptides, polypeptide fragments, variants and derivatives, fragments of the variants and derivatives, and analogs of the foregoing. In a preferred embodiment of this aspect of the invention there are provided methods of producing the aforementioned RG1 polypeptides comprising culturing host cells having expressibly incorporated therein an exogenously-derived RG1-encoding polynucleotide under conditions for expression of human RG1 in the host and then recovering the expressed polypeptide.

In accordance with another object of the invention there are provided products, compositions, processes and methods that utilize the aforementioned polypeptides and polynucleotides for inter alia research, biological, clinical and therapeutic purposes.

In accordance with certain preferred embodiments of this aspect of the invention, there are provided products, compositions and methods, inter alia, for assessing RG1 expression in cells by determining RG1 polypeptides or RG1-encoding mRNA; and assaying genetic variation and aberrations, such as defects, in rg1 genes.

In accordance with certain preferred embodiments of this and other aspects of the invention there are provided probes that hybridize to rg1 sequences.

It is a further object of the invention to provide antibodies which are highly selective for RG1 polypeptides, or fragments thereof, and which may be employed in a method for diagnosis and/or detection of RG1 expression, which may be associated with prostate cancer. In accordance with certain preferred embodiments of this aspect of the invention, antibodies are labeled in such a way as to produce a detectable signal. Particularly preferred would be an antibody labeled with a radiolabel, an enzyme, a chromophore or a fluorescer.

In a further aspect of the invention there are provided antibodies which are conjugated to a therapeutic agent for administration to cells in vitro, to cells ex vivo and to cells in vivo, or to a multicellular organism. Particularly preferred in this regard are therapeutic agents which are cytotoxic. In certain preferred embodiments in this regard is administration of such conjugated antibodies to a human patient for treatment of a disease state characterized by RG1 activity or expression such as prostate cancer.

In a further aspect of the invention, peptides and antiidiotypic antibodies are provided which can be used to stimulate an immune response.

In a further aspect of the invention there are provided ribozymes and polynucleotides complementary to rg1 polynucleotides (i.e. antisense polynucleotides) for administration to cells in vitro, to cells ex vivo and to cells in vivo, or to a multicellular organism. Particularly preferred in this regard is administration of antisense molecules to a human patient for treatment of a disease state, such as prostate cancer or benign prostatic hyperplasia, which is alleviated by decreasing the level of RG1 activity.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

FIG. 1: Polynucleotide sequence of rg1 (SEQ ID NO: 1), which encodes the biologically or immunologically active form of RG1.

FIG. 2: Deduced amino acid sequence of RG1 (SEQ ID NO: 2), with the F-spondin domains single underlined, and the thrombospondin domain double underlined.

FIG. 3: Amino acid alignment of RG1 (SEQ ID NO: 2) with the sequence of rat Mindin (SEQ ID NO: 13). The sequence of RG1 (SEQ ID NO: 2) is on the top.

FIG. 4: Polynucleotide (SEQ ID NO: 1) and deduced amino acid (SEQ ID NO: 2) sequences of RG1.

FIG. 7: Immunohistochemical staining of RG1 expression in human prostate tissues. Prostate tissues were obtained from the Urology Department at Stanford University School of Medicine. The staining was carried out using the Vector ABC-AP kit (AK5002). Staining was visualized with a Vector Red substrate kit (SK-5100) and counterstained with Hematoxylin. The results show strong peri-luminal membrane staining in gland formations.

DETAILED DESCRIPTION OF THE INVENTION

Definitions

Figure 5:
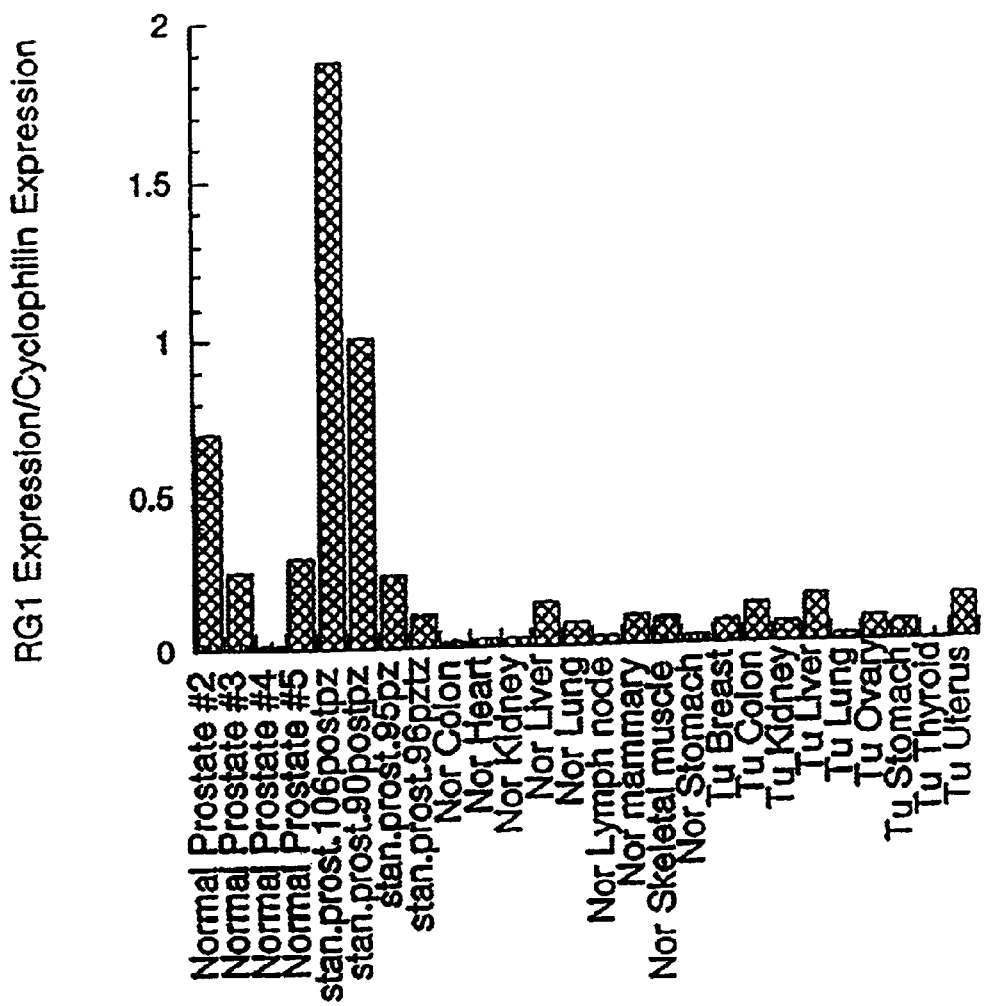
FIG. 5: Expression of rg1 mRNA in human tissues by Taqman based PCR analysis. RNA from human tissues, both tumor and normal, was isolated by standard techniques. Primers and probe to detect rg1 mRNA expression were designed using Perkin Elmer's Primer Express software and synthesized by Synthetic Genetics. Rg1 mRNA was detected in human prostate tissues. A much lower expression of rg1 mRNA could be detected in other tissues, e.g. liver.
Figure 6:
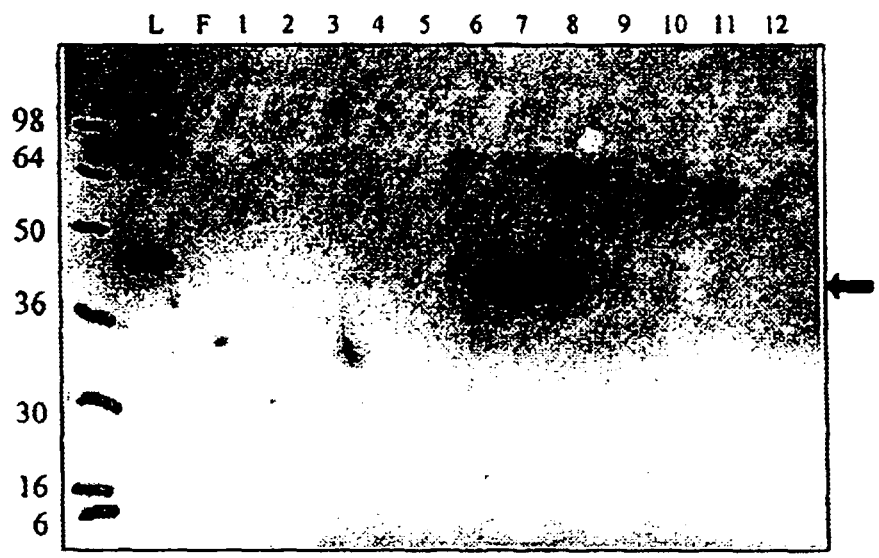
FIG. 6: Purification of native RG1 protein secreted by LNCaP cells. Western blot analysis, using antisera generated against a synthetic RG1 peptide sequence (3C, SEQ ID NO: 10; see Example 4), to detect native RG1 protein secreted from LNCaP cells. Elution fractions from Q-Sepharose chromatography of concentrated LNCaP cell conditioned media: (L) column load, (F) column flow-thru, (1–12) elution fractions across salt gradient. The predicted molecular weight of RG1 is ~36 kD, however the bacterially expressed RG1, BHK-expressed RG1 and the LNCaP-expressed RG1 protein all have been observed to migrate at ~45 kD on PAGE (L, fractions 6–9).

As used in the specification, examples and appended claims, unless specified to the contrary, the following terms have the meaning indicated.

"RG1" refers to the polypeptide having the amino acid sequence set out in FIG. 2 (SEQ ID NO: 2); variants, analogs, derivatives and fragments thereof, and fragments of the variants, analogs and derivatives. The terms "fragment," "derivative" and "analog" when referring to the polypeptide of FIG. 2 (SEQ ID NO: 2) mean a polypeptide which retains essentially the same biological and/or immunological activity as the polypeptide of FIG. 2 (SEQ ID NO: 2).

"rg1" refers to the polynucleotide having the sequence set out in FIG. 1 (SEQ ID NO: 1) and polynucleotides encoding polypeptides having the amino acid sequence of RG1 set out in FIG. 2 (SEQ ID NO: 2); and to polynucleotides encoding RG1 variants, analogs, derivatives and fragments, and fragments of the variants, analogs and derivatives. Rg1 also refers to such polynucleotides composed of RNA as well as to polynucleotides which are the complement of polynucleotides which encode the polypeptide sequence set out in FIG. 2 (SEQ ID NO: 2).

"Polynucleotide(s)" generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term "polynucleotide" includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritium-labelled bases, to name just two examples, are polynucleotides as the term is used herein.

It will be appreciated that a great variety of modifications have been made to DNA and RNA that serve many useful purposes known to those of skill in the art. The term "polynucleotide" as it is employed herein embraces such chemically, enzymatically or metabolically modified forms of polynucleotides, as well as the chemical forms of DNA and RNA characteristic of viruses and cells, including simple and complex cells, inter alia.

"Polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, I. E. Creighton, *Proteins-Structure and Molecular Properties,* 2nd Ed., W. H. Freeman and Company, New York, 1993. Many detailed reviews are available on this subject, such as, for example, those provided by Wold, F., in *Posttranslational Covalent Modification of Proteins,* B. C. Johnson, Ed., Academic Press, New York, pp 1–12, 1983; Seifter et al., *Meth. Enzymol.* 182: 626–646, 1990 and Rattan et al., *Protein Synthesis: Posttranslational Modifications and Aging,* Ann. N.Y. Acad. Sci. 663: 48–62, 1992.

It will be appreciated, as is well known and as noted above, that polypeptides are not always entirely linear. For instance, polypeptides may be branched as a result of ubiquitination, and they may be circular, with or without branching, generally as a result of posttranslational events, including natural processing events and events brought about by human manipulation which do not occur naturally Circular, branched and branched circular polypeptides may be synthesized by non-translational natural processes and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli,* prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli.* Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation, inter alia. Similar considerations apply to other modifications.

It will be appreciated that the same type of modification may be present to the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

"Polynucleotide encoding a polypeptide" as used herein encompasses polynucleotides which include a sequence encoding a polypeptide of the present invention, particularly the RG1 polypeptide having the amino acid sequence set out in FIG. 2 (SEQ ID NO: 2). The term encompasses polynucleotides that include a single continuous region or discontinuous regions encoding the polypeptide (for example, interrupted by introns) together with additional regions.

"Biological activity" refers to the structural, regulatory or biochemical functions of naturally occurring RG1 polypeptide.

"Immunologic activity" refers to the capability of the natural, recombinant or synthetic RG1, or any fragment thereof, to induce a specific immune response in appropriate animals or cells and to bind with specific antibodies.

"Oligonucleotide(s)" refers to relatively short polynucleotides. Often the term refers to single-stranded deoxyribonucleotides but it can refer as well to single- or double-stranded ribonucleotides, RNA DNA hybrids and double-stranded DNAs, among others. Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms. "Oligonucleotides" or "oligomers" or polynucleotide "fragment", "portion", or "segment" refers to a polynucleotide sequence of at least about 10 nucleotides and as many as about 60 nucleotides, preferably about 15 to 30 nucleotides, and more preferably about 20–25 nucleotides.

"Naturally occurring RG1" refers to RG1 produced by human cells that have not been genetically engineered and specifically contemplates various RG1 forms arising from post-translational modifications of the polypeptide including but not limited to acetylation, carboxylation, glycosylation, phosphorylation, lipidation, acylation, and cleavage.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in polynucleotide sequence from another, reference polynucleotide. Generally, differences are limited so that the polynucleotide sequences of the reference and the variant are closely similar overall and, in many regions, identical.

As noted below, changes in the polynucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the polynucleotide sequence of the variant may alter the amino acid sequence of a polypeptide encoded by the reference polynucleotide. Such polynucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. Recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced to modify the properties of the polypeptide, to change ligand-binding affinities, interchain affinities, or polypeptide degradation or turnover rate.

"Allelic variant" refers to an alternative form of the rg1 polynucleotide. Alleles result from a mutation, i.e., a change in the polynucleotide sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of nucleotides. Each of these types of changes may occur alone, or in combination with the others, or one or more times in a given sequence.

"Derivative" refers to polynucleotides or polypeptides derived from naturally occurring rg1 or RG1, respectively, by chemical modifications such as ubiquitination, labeling (e.g., with radionuclides, various enzymatic modifications), pegylation (derivatization with polyethylene glycol) or by insertion or substitution of amino acids such as ornithine (or substitution of the nucleotides which code for such as an amino acid), which do not normally occur in human proteins.

"Deletion" is defined as a change in either polynucleotide or amino acid sequences in which one or more polynucleotides or amino acid residues, respectively, are absent.

"Insertion" or "addition" is that change in a polynucleotide or amino acid sequence which has resulted in the addition of one or more polynucleotides or amino acid residues, respectively, as compared to the naturally occurring polynucleotide or amino acid sequence.

"Substitution" results from the replacement of one or more polynucleotides or amino acids by different polynucleotides or amino acids, respectively.

Preferably, amino acid substitutions are the result of replacing one amino acid with another amino acid having similar structural and/or chemical properties, such as the replacement of a leucine with an isoleucine or valine, an aspartate with a glutamate, or a threonine with a serine, i.e. conservative amino acid replacement. Insertions or deletions are typically in the range of about 1 to 5 amino acids. The variation allowed may be experimentally determined by systematically making insertions, deletions, or substitutions of amino acids in the polypeptide using recombinant DNA techniques and assaying the resulting recombinant variants for activity.

"Fragment" is a polypeptide having an amino acid sequence that entirely is the same as part but not all of the amino acid sequence of the aforementioned RG1 polypeptides and variants or derivatives thereof.

A polypeptide "fragment", "portion", or "segment" is a stretch of amino acid residues of at least about 5 amino acids, often at least about 7 amino acids, typically at least about 9 to 13 amino acids, and in various embodiments, at least about 17 or more amino acids.

"Recombinant" or "recombinant DNA molecule" refers to a polynucleotide sequence which is not naturally occurring, or is made by the artificial combination of two otherwise separated segments of sequence. By "recombinantly produced" is meant artificial combination often accomplished by either chemical synthesis means, or by the artificial manipulation of isolated segments of polynucleotides, e.g., by genetic engineering techniques. Such manipulation is usually done to replace a codon with a redundant codon encoding the same or a conservative amino acid, while typically introducing or removing a sequence recognition site. Alternatively, it is performed to join together polynucleotide segments with desired functions to generate a single genetic entity comprising a desired combination of functions not found in the common natural forms. Restriction enzyme recognition sites, regulation sequences, control sequences, or other useful features may be incorporated by design. "Recombinant DNA molecules" include cloning and expression vectors. "Recombinant" may also refer to a polynucleotide which encodes a polypeptide and is prepared using recombinant DNA techniques.

"Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. For example, with respect to polynucleotides, the term isolated means that it is separated from the chromosome and cell in which it naturally occurs. Polynucleotides and polypeptides may occur in a composition, such as media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

"Substantially pure" and "substantially homogenous" are used interchangeably and describe RG1 polypeptide, or fragments thereof, or a polynucleotide segment encoding same, where such polypeptide or polynucleotide is separated from components that naturally accompany it. An RG1 polypeptide or fragment thereof, or DNA segment encoding same is substantially free of naturally-associated components when it is separated from the native contaminants which accompany it in its natural state. Thus, a polypeptide that is chemically synthesized or synthesized in a cellular system different from the cell in which it naturally originates will be substantially free from its naturally-associated components. Similarly, a polynucleotide that is chemically synthesized or synthesized in a cellular system different from the cell in which it naturally originated will be substantially free from its naturally-associated components.

"Homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides.

"Similarity", when used to describe a polypeptide, is determined by comparing the amino acid sequence and the conserved amino acid substitutes of one polypeptide to the sequence of a second polypeptide "Polymerase chain reaction" or "PCR" refers to a procedure wherein specific pieces of DNA are amplified as described in U.S. Pat. No. 4,683,195, issued Jul. 28, 1987. Generally, sequence information from the ends of the polypeptide fragment of interest or beyond needs to be available, such that oligonucleotide primers can be designed; these primers will point towards one another, and will be identical or similar in sequence to opposite strands of the template to be amplified. The 5' terminal nucleotides of the two primers will coincide with the ends of the amplified material. PCR can be used to amplify specific DNA sequences from total genomic DNA, cDNA transcribed from total cellular RNA, plasmid sequences, etc. (See generally Mullis et al., *Cold Spring Harbor Symp. Quant Biol.*, 51: 263, 1987; Erlich, ed., *PCR Technology*, Stockton Press, NY, 1989).

"Stringency" typically occurs in a range from about $T_m$ (melting temperature)-5° C. (5° below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. As herein used, the term "stringent conditions" means hybridization will occur only if there is at least 95% and preferably at least 97% identity between the sequences.

"Hybridization" as used herein, shall include "any process by which a polynucleotide strand joins with a complementary strand through base pairing" (Coombs, J., *Dictionary of Biotechnology*, Stockton Press, New York, N.Y., 1994).

"Therapeutically effective dose" refers to that amount of polypeptide or its antibodies, antagonists, or inhibitors, including antisense molecules and ribozymes, which ameliorate the symptoms or conditions of a disease state. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$.

"Treating" or "treatment" as used herein covers the treatment of a disease-state in a human patient, which disease-state is associated with prostate tumor growth and includes disease states in which the patient is in need of decreased levels of RG1.

DETAILED DESCRIPTION OF THE INVENTION

The present invention relates to novel RG1 polypeptides, rg1 polynucleotides, and antibodies directed toward RG1 polypeptides, among other things, as described in greater detail below. In particular, the invention relates to novel RG1 polypeptides and the polynucleotides encoding these RG1 polypeptides, and relates especially to RG1 having the amino acid sequence set out in FIG. 2 (SEQ ID NO: 2) and rg1 having the polynucleotide sequence set out in FIG. 1 (SEQ ID NO: 1). The present invention also encompasses RG1 variants. A preferred RG1 variant is one having at least 70% similarity (preferably at least 70% identity) to the polypeptide sequence shown in FIG. 2 (SEQ ID NO: 2) and more preferably at least 90% similarity (more preferably at least 90% identity) to the polypeptide shown in FIG. 2 (SEQ ID NO: 2) and still more preferably at least 95% similarity (still more preferably at least 95% identity) to the polypeptide sequence shown in FIG. 2 (SEQ ID NO: 2) and also includes portions of such polypeptides with such portion of the polypeptide generally containing at least 30 amino acids and more preferably at least 50 amino acids.

The coding sequence for the predicted RG1 polypeptide begins 296 base pairs from the 5' end of the nucleotide sequence shown in FIG. 1 (SEQ ID NO: 1). RG1 contains three structural domains characteristic of Mindin/F-spondin superfamily of extracellular matrix proteins: two spondin domains (FS1 and FS2), comprising amino acids 31 to 103 and 138 to 221, respectively, and a thrombospondin domain, comprising amino acids 278 to 330.

The present invention is based in part on the structural homology shown in FIG. 3 between RG1 (SEQ ID NO: 2) and rat Mindin (SEQ ID NO: 13), another member of the extracellular matrix protein family. The amino acid sequence of RG1 (SEQ ID NO: 2) is approximately 89.7% similar to rat Mindin (SEQ ID NO: 13).

The present invention is also based in part on the expression profile of RG1, as demonstrated by its expression in prostate tissue libraries and over-expression in prostate tumor libraries. This tissue profile is seen in analysis of mRNA expression in tissue samples from normal and tumor tissues by PCR-based Taqman analysis. This method of analysis demonstrated that mRNA encoding RG1 is over-expressed in prostate tissues as compared with other tissues.

Polynucleotides

In accordance with one aspect of the present invention, there are provided isolated polynucleotides that encode the RG1 polypeptide having the deduced amino acid sequence of FIG. 2 (SEQ ID NO: 2).

Using the information provided herein, such as the polynucleotide sequence set out in FIG. 1 (SEQ ID NO: 1), a polynucleotide of the present invention encoding a RG1 polypeptide may be obtained using standard cloning and screening procedures, such as those for cloning cDNAs using mRNA from cells of human tissue as starting material. Illustrative of the invention, the polynucleotide sequence in FIG. 1 (SEQ ID NO: 1) was found in cDNA clones obtained from human prostate tissues. Rg1 was identified as a gene expressed in the prostate by mining Incyte's LifeSeq database. The nucleotide sequence was identified by an annotation search of the database, using the "Protein Function" tool provided by Incyte for the purpose of searching the database. The nucleotide sequence was found in the category of cell adhesion molecules in the annotated database and was described as a homologue of f-spondin Electronic Northern analysis of the distribution of rg1 polynucleotide sequences in the set of libraries in the database revealed that rg1 was expressed at high levels in the prostate libraries and at lower levels in a number of other tissue libraries, including those from normal and tumor tissues.

Following assembly of the set of rg1 clones in the database into a contiguous polynucleotide sequence, and editing of the contiguous sequence, a full-length coding sequence was identified in the predicted assembled polynucleotide. This sequence coded for a protein with homology to rat mindin.

Incyte clones 1640796, 1712252, and 1880265 were obtained from Incyte for experimental work and clone 3360733 was identified as containing the most 5' nucleotide sequence. This clone was fully sequenced and contained the full coding sequence for the predicted RG1 protein. This sequence is shown in FIG. 1 (SEQ D NO: 1).

Polynucleotides of the present invention may be in the form of RNA, such as mRNA, or in the form of DNA, including, for instance, cDNA and genomic DNA obtained by cloning or produced by chemical synthetic techniques or by a combination thereof, or by methods described herein. The DNA may be double-stranded or single-stranded. Single-stranded DNA may be the coding strand, also known as the sense strand, or it may be the non-coding strand, also referred to as the anti-sense strand.

The sequence which encodes the polypeptide may be identical to the coding sequence of the polynucleotide shown in FIG. 1 (SEQ ID NO: 1). It also may be a polynucleotide with a different sequence, which, as a result of the redundancy (degeneracy) of the genetic code, encodes the polypeptide of FIG. 2 (SEQ ID NO: 2).

Polynucleotides of the present invention which encode the polypeptide of FIG. 2 (SEQ ID NO: 2) may include, but are not limited to, the coding sequence for the polypeptide itself; the coding sequence of the polypeptide, together with additional, non-coding sequences, including for example, but not limited to, introns and non-coding 5' and 3' sequences, such as the transcribed, non-translated sequences that play a role in transcription, mRNA processing (for example, splicing and polyadenylation signals) or additional coding sequences which code for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pTrcHisB vector (Invitrogen, Carlsbad, Calif.) among others, many of which are commercially available. As described in Gentz et al. (*Proc. Natl. Acad. Sci., USA* 86: 821–824, 1989), for instance, hexa-histidine provides for convenient purification of the fusion protein.

The polynucleotides may encode a polypeptide which is the polypeptide plus additional amino or carboxyl-terminal amino acids, or amino acids interior to the polypeptide (when the active form has more than one polypeptide chain, for instance). Such sequences may play a role in processing of a polypeptide from precursor to final form, may facilitate polypeptide trafficking, may prolong or shorten polypeptide half-life or may facilitate manipulation of a polypeptide for assay or production, among other things. As generally is the case in situ, the additional amino acids may be processed away from the polypeptide by proteolytic enzymes.

The present invention further relates to variants of the herein above described polynucleotides which encode for fragments, analogs and derivatives of the polypeptide having the deduced amino acid sequence of FIG. 2 (SEQ ID NO: 2). A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by polynucleotide substitutions, deletions or additions. The substitutions, deletions or additions may involve one or more polynucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of RG1 set out in FIG. 2 (SEQ ID NO: 2); variants, analogs, derivatives and fragments thereof, and fragments of the variants, analogs and derivatives Further particularly preferred in this regard are polynucleotides encoding RG1 variants, analogs, derivatives and fragments, and variants, analogs and derivatives of the fragments, which have the amino acid sequence of the RG1 polypeptide of FIG. 2 (SEQ ID NO: 2) in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the RG1 polypeptide. Also especially preferred in this regard are conservative substitutions. Most highly preferred are polynucleotides encoding polypeptides having the amino acid sequence of FIG. 2 (SEQ ID NO. 2) without substitutions.

Further preferred embodiments of the invention are polynucleotides that are at least 70% identical to a polynucleotide encoding the RG1 polypeptide having the amino acid sequence set out in FIG. 2 (SEQ ID NO: 2), and polynucleotides which are complementary to such polynucleotides. Alternatively, most highly preferred are polynucleotides that comprise a region that is at least 80% identical to a polynucleotide encoding the RG1 polypeptide and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these, those with at least 98% and at least 99% are particularly highly preferred, with at least 99% being the more preferred.

Particularly preferred embodiments in this respect, moreover, are polynucleotides which encode polypeptides which retain substantially the same biological activity as the polypeptide encoded by the polynucleotide sequence of FIG. 1 (SEQ ID NO: 1).

The present invention further relates to polynucleotides that hybridize to the herein above-described sequences. In this regard, the present invention especially relates to polynucleotides which hybridize under stringent conditions to the herein above-described polynucleotides.

As discussed additionally herein regarding polynucleotide assays of the invention, for instance, polynucleotides of the invention as discussed above, may be used as a hybridization probes for cDNA and genomic DNA to isolate full-length cDNAs and genomic clones encoding RG1 and to isolate cDNA and genomic clones of other genes that have a high sequence similarity to the rg1 gene Such probes generally will comprise at least 15 bases. Preferably, such probes will have at least 30 bases and may have at least 50 bases.

For example, the coding region of the rg1 gene may be isolated by screening libraries using synthetic oligonucleotide probes that have been designed using the known DNA sequence. For example, a labeled oligonucleotide having a sequence complementary to that of a polynucleotide of the present invention can be used to screen a library of cDNA or genomic DNA to identify clones that hybridize to the probe.

In sum, a polynucleotide of the present invention may encode a polypeptide, a polypeptide plus a leader sequence (which may be referred to as a prepolypeptide).

It will be appreciated that the invention also relates to, among others, polynucleotides encoding the polypeptide fragments, polynucleotides that hybridize to polynucleotides encoding polypeptide fragments, particularly those that hybridize under stringent conditions, and polynucleotides, such as PCR primers, for amplifying polynucleotides that encode polypeptide fragments. In these regards, preferred polynucleotides are those that correspond to preferred polypeptide fragments, as discussed below.

Polypeptides

The present invention further relates to a RG1 polypeptide which has the deduced amino acid sequence of FIG. 2 (SEQ ID NO: 2).

The invention also relates to fragments, analogs and derivatives of these polypeptides. The terms fragment, derivative and analog when referring to the polypeptide of FIG. 2 (SEQ ID NO: 2) means a polypeptide which retains essentially the same biological activity as such a polypeptide.

The polypeptide of the present invention may be a recombinant polypeptide, a natural polypeptide or a synthetic polypeptide. In certain preferred embodiments, it is a recombinant polypeptide.

The fragment, derivative or analog of the polypeptide of FIG. 2 (SEQ ID NO: 2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol) or (iv) one in which the additional amino acids are fused to the polypeptide, such as a leader or secretory sequence or a sequence which is employed for purification of the polypeptide. Such fragments, derivatives and analogs are deemed to be within the scope of those skilled in the art from the teachings herein.

Among the particularly preferred embodiments of the invention in this regard are polypeptides having the amino acid sequence of RG1 set out in FIG. 2 (SEQ ID NO: 2), variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile, interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further particularly preferred in this regard are variants, analogs, derivatives and fragments, and variants, analogs and derivatives of the fragments, having the amino acid sequence of the RG1 polypeptide of FIG. 2 (SEQ ID NO: 2) in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the RG1 polypeptide. Also especially preferred in this regard are conservative substitutions. Most highly preferred are polypeptides having the amino acid sequence of FIG. 2 (SEQ ID NO: 2) without substitutions.

The polypeptides and polynucleotides of the present invention are preferably provided in an isolated form, and preferably are purified to homogeneity.

The polypeptides of the present invention also include the polypeptide of FIG. 2 (SEQ ID NO: 2) as well as polypeptides which have at least 70% similarity (preferably at least 70% identity) to the polypeptide of FIG. 2 (SEQ ID NO: 2) and more preferably at least 90% similarity (more preferably at least 90% identity) to the polypeptide of FIG. 2 (SEQ ID NO: 2) and still more preferably at least 95% similarity (still more preferably at least 95% identity) to the polypeptide of FIG. 2 (SEQ ID NO: 2) and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptides by peptide synthesis; therefore, the fragments may be employed as intermediates for producing the full-length polypeptides.

Fragments

Also among preferred embodiments of this aspect of the present invention are polypeptides comprising fragments of RG1, most particularly fragments of the RG1 of FIG. 2 (SEQ ID NO: 2), and fragments of variants and derivatives of the RG1 of FIG. 2 (SEQ ID NO: 2).

In this regard a fragment is a polypeptide having an amino acid sequence that entirely is the same as part but not all of the amino acid sequence of the aforementioned RG1 polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of an RG1 polypeptide of the present invention comprised within a precursor polypeptide designed for expression in a host and having heterologous pre- and propolypeptide regions fused to the amino terminus of the RG1 fragment and an additional region fused to the carboxyl terminus of the fragment. Therefore, fragments in one aspect of the meaning intended herein, refers to the portion or portions of a fusion polypeptide or fusion protein derived from RG1.

As representative examples of polypeptide fragments of the invention, there may be mentioned those which have from about 25 to about 331 amino acids.

In this context "about" includes the particularly recited range and ranges larger or smaller by several, a few, 5, 4, 3, 2 or 1 amino acid at either extreme or at both extremes. For instance, about 331 amino acids in this context means a polypeptide fragment of 25 plus or minus several, a few, 5, 4, 3, 2 or 1 amino acids to 331 plus or minus several a few, 5, 4, 3, 2 or 1 amino acid residues, i.e., ranges as broad as 25 minus several amino acids to 331 plus several amino acids to as narrow as 25 plus several amino acids to 331 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions Most highly preferred of all in this regard are fragments from about 25 to about 331 amino acids.

Among especially preferred fragments of the invention are truncation mutants of RG1. Truncation mutants of RG1 include variants or derivatives of the sequence of FIG. 2 (SEQ ID NO: 2), except for deletion of a continuous series of residues (that is, a continuous region, part or portion) that includes the amino terminus of the sequence shown in FIG. 2 (SEQ ID NO: 2), or a continuous series of residues that includes the carboxyl terminus or, as in double truncation mutants, deletion of two continuous series of residues, one including the amino terminus and one including the carboxyl terminus. Fragments having the size ranges set out above also are preferred embodiments of truncation fragments, which are especially preferred among fragments generally.

Especially preferred in this aspect of the invention are fragments characterized by biological and/or immunological attributes of RG1. Such fragments include those containing the predicted structural domains of RG1, which encompass at least amino acid 31 to 103, 138 to 221 and 278 to 330 or those fragments used to generate antibodies, such as those described in Example 4.

Certain preferred regions in these regards are set out in FIG. 2 (SEQ ID NO: 2), and include, but are not limited to, regions of the aforementioned types identified by analysis of the amino acid sequence set out in FIG. 2 (SEQ ID NO: 2).

Among highly preferred fragments in this regard are those that comprise regions of RG1 that combine several structural features, such as the features set out above. In this regard, the two spondin and one thrombospondin domains, encompassing about amino acids 31 to 103, 138 to 221, and 278 to 330, respectively, which are characteristic of the Mindin/spondin superfamily of extracellular matrix proteins, are especially preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of RG1. Most highly preferred in this regard are fragments that have a chemical, biological or other activity of RG1, including those with a similar activity or an improved activity, or with a decreased undesirable activity. Highly preferred in this regard are fragments that contain regions that are homologs in sequence, or in position, or in both sequence and position to active regions of related polypeptides, such as the other proteins of the Mindin family, which includes RG1.

Vectors, Host Cells, and Expression Systems

The present invention also relates to vectors which include polynucleotides of the present invention, host cells which are genetically engineered with vectors of the invention and the production of polypeptides of the invention by recombinant techniques. Such techniques are described in Sambrook et al., *Molecular Cloning, A Laboratory Manual,* Cold Spring Harbor Press, Plainview, N.Y., 1989 and Ausubel, F. M. et al., *Current Protocols in Molecular Biology,* John Wiley & Sons, New York, N.Y., 1989.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case, the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques. In accordance with this aspect of the invention, the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors, also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter al/ia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses, retroviruses, and alphavirues such as Sindbis virus, and vectors derived from combinations thereof, such as those derived from plasmid and bacteriophage genetic elements such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those of skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the E. coli lac, trp, tac, and trc promoters, the SV40 early and late promoters and promoters of retroviral LTRs to name just a few of the well-known promoters. It will be understood that numerous promoters not mentioned are suitable for use in this aspect of the invention, are well known and may readily be employed by those of skill in the manner illustrated by the discussion and the examples herein.

In general, expression constructs will contain sites for transcription initiation and termination and, in the transcribed region, a ribosome binding site for translation. The coding portion of the transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose In this regard, the expression vectors preferably contain one or more selectable marker genes to provide a phenotypic trait for selection of transformed host cells. Preferred markers include dihydrofolate reductase, neomycin, puromycin, or hygromycin resistance for eukaryotic cell culture, and tetracycline, theomycin, kanamycin or ampicillin resistance genes for culturing E. coli and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as E. coli. Streptomyces and Salmonella typhimurium cells; fungal cells, such as yeast cells; insect cells such as Drosophila S2 and Spodoptera Sf9 cells; animal cells such as CHO, COS and Bowes melanoma cells, and plant cells, preferably insect cells BTI-TN-5B1-4. Hosts for a great variety of expression constructs are well known, and those of skill will be enabled by the present disclosure readily to select a host for expressing a polypeptides in accordance with this aspect of the present invention.

Various mammalian cell culture systems can be employed for expression, as well. Examples of mammalian expression systems include the COS-7 lines of monkey kidney fibroblast (Gluzman et al., Cell 23: 175, 1991). Other cell lines capable of expressing a compatible vector include for example, the C127, 3T3, CHO, HeLa, human kidney 293 and BHK cell lines. In mammalian host cells, a number of viral-based expression systems may be utilized. In cases where an adenovirus is used as an expression vector, the polynucleotide sequence coding for RG1 may be ligated into an adenovirus transcription/translation complex consisting of the late promoter and tripartite leader sequence. Insertion in a nonessential E1 or E3 region of the viral genome will result in a viable virus capable of expressing RG1 in infected host cells (Logan and Shenk, Proc. Natl. Acad. Sci. USA 81:3655–59, 1984). In addition, transcription enhancers, such as the Rous sarcoma virus (RSV) enhancer, may be used to increase expression in mammalian host cells.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE7O, pQE6O and pQE-9, available from Qiagen USA (Valencia, Calif.), pBS vectors, Phagescript® vectors, Bluescript® vectors, pNH8A, pNHI6a, pNHI8A, pNH46A, available from Stratagene (LaJolla, Calif.); and ptrc99a, pK223–3, pKK233-3, pDR540, pRIT5 available from Pharmacia Biotech (Piscataway, N.J.). Most preferred is the pTrcHisB vector, available from Invitrogen. Among preferred eukaryotic vectors are pWLNEO, pSV2CAT, pOG44, PXTI and pSG available from Stratagene; and PSVK3, pBPV, pMSG and pSVL available from Pharmacia Biotech. Most preferred is the pClneo vector available from Promega. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("cat") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-B and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the *E. coli* lad and lacZ promoters, the T3 and T7 promoters, the T5 tac promoter, the lambda PR, PL promoters, the trp promoter, and the trc hybrid promoter, which is derived from the trp and lac promoters. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV") and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

Generally, recombinant expression vectors will include origins of replication, a promoter derived from a highly-expressed gene to direct transcription of a downstream structural sequence, and a selectable marker to permit isolation of vector containing cells after exposure to the vector.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell. Constructs in host cells can be used in a conventional manner to produce the gene product encoded by the recombinant sequence.

Polypeptides can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., cited elsewhere herein.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals. The polypeptide may be expressed in a modified form, such as a fusion protein, and may include not only secretion signals but also additional heterologous fuctional regions Thus for instance, a region of additional amino acids, particularly charged amino acids, may be added to the N-terminus of the polypeptide to improve stability and persistence in the host cell, during purification or during subsequent handling and storage. Also, special regions also may be added to the polypeptide to facilitate purification. Such regions may be removed prior to final preparation of the polypeptide The addition of peptide moieties to polypeptides to engender secretion or excretion, to improve stability and to facilitate purification, among others, are familiar and routine techniques in the art For example, when large quantities of RG1 are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the rg1 coding sequence may be ligated into the vector in frame with sequence for the amino-terminal Met and the subsequent 7 residues of β-galactosidase so that a hybrid protein is produced; pIN vectors (Van Heede and Shuster, *J. Biol. Chem.* 264–5503–5509, 1989) and the like. PTrcHis vectors (Invitrogen, Carlsbad, Calif.) may be used to express foreign polypeptides as fusion proteins containing a polyhistidine (6xHis) tag for rapid purification. Proteins made in such systems are designed to include cleavage sites, such as an enterokinase cleavage site, so that the cloned polypeptide of interest can be released from the fusion peptide moiety at will.

Following transformation of a suitable host strain and growth of the host strain to an appropriate cell density, inducible promoters, if present, can be induced by appropriate means (e.g., temperature shift or exposure to chemical inducer) and cells cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

The RG1 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification. Various other methods of protein purification well known in the art include those described in Deutscher, M., *Methods in Enzymology,* Vol 182, Academic Press, San Diego, 1982; and Scopes, R., *Protein Purification: Principles and Practice* Springer-Verlag, New York, 1982.

Alternatively, the polypeptides of the present invention can be produced by direct peptide synthesis using solid-phase techniques (Stewart et al., *Solid-Phase Peptide Synthesis,* W. H. Freeman Co., San Francisco, 1969; Merrifield, J., *J. Am. Chem. Soc.* 85:2149–2154, 1963). In vitro protein synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Various fragments of RG1 may be chemically synthesized separately and combined using chemical methods to produce the full length molecule.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Uses of RG1 Polypeptides and the Polynucleotides which Encode Them

Rg1 polynucleotides and RG1 polypeptides may be used in accordance with the present invention for a variety of applications, particularly those that make use of the chemical and biological properties of RG1. Additional applications relate to diagnosis and to treatment of diseases of cell proliferation, such as prostate cancer. These aspects of the invention are illustrated further by the following discussion and are described further within the body of the specification.

The rationale for the use of the polynucleotide and polypeptide sequences of the present invention is based in part on the chemical and structural homology between the RG1 disclosed herein and other extracellular matrix molecules and on the preferential expression of RG1 in prostate tissues as compared with other tissues. RG1 may be used in the diagnosis and treatment of conditions, disorders or diseases associated with inappropriate growth of prostate tissue. These would include, but are not limited to, cancer and metastatic tumor growth.

Rg1 polynucleotide sequences can be used as DNA probes, and as targets for antisense and ribozyme therapy, or as templates for the production of antisense polynucleotides.

RG1 polypeptides can be used to generate antibodies to RG1 that may be useful in detecting the levels of RG1 polypeptide in cells and tissues and in targeting drugs to primary and metastatic tumors.

RG1 polypeptides may be used to stimulate an immune response to RG1 containing cells.

Polynucleotides encoding RG1 may be useful in diagnostic assays for detecting the levels of polynucleotides encoding RG1 in cells and tissues.

In conditions associated with expression of RG1, such as prostate cancer, it may be advantageous to suppress expression or activity of RG1. RG1 expression could be suppressed by administration of antisense oligonucleotides or ribozymes. Alternatively, antibodies specifically recognizing areas of the RG1 polypeptide which are responsible for its activity may be administered to treat diseases or conditions associated with RG1 activity.

Polynucleotide Assays

This invention is also related to the use of the rg1-related polynucleotides to detect complementary polynucleotides such as, for example, as a diagnostic reagent. Detection of rg1 polynucleotides associated with a disease state will provide a tool for the development of in vitro and in vivo diagnostics that can add or define a diagnosis of a disease or susceptibility to a disease that results from tissue specific expression of RG1.

Individuals carrying mutations in the gene encoding RG1 may be detected at the DNA level by a variety of techniques. Polynucleotide samples for diagnosis may be obtained from a patient's cells, such as from blood, urine, saliva, tissue biopsy and autopsy material. The genomic DNA may be used directly for detection or may be amplified enzymatically by using PCR prior to analysis (Saiki et al., *Nature,* 324 163–166, 1986). RNA or cDNA may also be used in the same ways. As an example, PCR primers complementary to the polynucleotide sequence encoding RG1 can be used to identify and analyze rg1 expression and mutations. For example, deletions and insertions can be detected by a change in size of the amplified product in comparison to the normal genotype. Point mutations can be identified by hybridizing amplified DNA to radiolabeled rg1 RNA or alternatively, radiolabeled rg1 antisense DNA sequences. Perfectly matched sequences can be distinguished from mismatched duplexes by RNase A digestion or by differences in melting temperatures Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled polynucleotide or by automatic sequencing procedures with fluorescent tags Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230: 1242, 1985).

Sequence changes at specific locations also may be revealed by nuclease protection assays, such as RNase and S1 protection or the chemical cleavage method (e.g., Catton et al., *Proc. Natl. Acad. Sci., USA*, 85:4397–4401, 1985).

Thus, the detection of a specific DNA sequence may be achieved by methods such as hybridization, RNase protection, chemical cleavage, direct DNA sequencing or the use of restriction enzymes, (e.g, restriction fragment length polymorphisms ("RFLP") and Southern blotting of genomic DNA).

In addition to more conventional gel-electrophoresis and DNA sequencing, mutations also can be detected by in situ analysis.

Polypeptide Assays

The present invention also relates to diagnostic assays such as quantitative and diagnostic assays for detecting levels of RG1 polypeptide in cells and tissues and body fluids, including determination of normal and abnormal levels. Thus, for instance, a diagnostic assay in accordance with the invention for detecting over-expression of RG1 polypeptide compared to normal control tissue samples may be used to detect the presence of neoplasia, for example, prostate cancer. Such diagnostic tests may be used to detect metastatic tumor growth, as well. Assay techniques that can be used to determine levels of a polypeptide, such as a RG1 polypeptide of the present invention, in a sample derived from a host are well-known to those of skill in the art. Such assay methods include radioimmunoassays (RIA), competitive-binding assays, western Blot analysis and enzyme-linked immunoabsorbant assays (ELISA), and fluorescent activated cell sorting (FACS) Among these ELISAs frequently are preferred. An ELISA assay initially comprises preparing an antibody specific to RG1, preferably a monoclonal antibody. In addition a reporter antibody generally is prepared which binds to the monoclonal antibody. The reporter antibody is attached to a detectable reagent such as a radioactive, fluorescent or enzymatic reagent, in this example horseradish peroxidase enzyme.

To carry out an ELISA a sample is removed from a host and incubated on a solid support, e.g. a polystyrene dish, that binds the polypeptides in the sample. Any free polypeptide binding sites on the dish are then covered by incubating with a non-specific protein such as bovine serum albumin. Next, the monoclonal antibody is incubated in the dish during which time the monoclonal antibodies attach to any RG1 polypeptides attached to the polystyrene dish. Unbound monoclonal antibody is washed out with buffer The reporter antibody linked to horseradish peroxidase is placed in the dish resulting in binding of the reporter antibody to any monoclonal antibody bound to RG1. Unattached reporter antibody is then washed out. Reagents for peroxidase activity, including a calorimetric substrate are then added to the dish. Immobilized peroxidase, linked to RG1 through the primary and secondary antibodies, produces a colored reaction product. The amount of color developed in a given time period indicates the amount of RG1 polypeptide present in the sample. Quantitative results typically are obtained by reference to a standard curve.

A competition assay may be employed wherein antibodies specific to RG1 are attached to a solid support and labeled RG1 and a sample derived from the host are passed over the solid support and the amount of label detected attached to the solid support can be correlated to a quantity of RG1 in the sample.

These and other assays are described, among other places, in Hampton et al. (*Serological Methods, a Laboratory Manual, APS Press,* St Paul, Minn., 1990) and Maddox et al. (*J. Exp. Med.* 158:12111, 1983).

Antibodies

The invention further relates to antibodies that specifically bind to RG1, herein referred to as RG1 antibodies. The over-expression of RG1 in prostate tissues and its cell surface location represent characteristics of an excellent marker for screening, diagnosis, prognosis, follow-up assays and imaging methods. In addition, these characteristics indicate that RG1 may be an excellent target for therapeutic methods such as targeted antibody therapy, immunotherapy, and gene therapy. As used herein, the term "specifically binds to" refers to the interaction of an antibody and a polypeptide, in which the interaction is dependent upon the presence of a particular structure (i.e., the antigenic determinant or epitope) on the polypeptide; in other words, the antibody is recognizing and binding to a specific polypeptide structure rather than to proteins in general.

The RG1 polypeptides, their fragments or other derivatives, or analogs thereof, or cells expressing them can be used as an immunogen to produce antibodies thereto (Harlow, Antibodies, Cold Spring Harbor Press, NY (1989)). These antibodies can be, for example, polyclonal or monoclonal antibodies. The present invention also includes chimeric, single chain, humanized, and human antibodies, as well as Fab fragments, or the product of a Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, *Nature* 256: 495–497, 1975), the human B-cell hybridoma technique (Kozbor et al, *Immunology Today* 4: 72,1983) and the EBV-hybridoma technique to produce human monoclonal antibodies (Cole et al., in *Monoclonal Antibodies and Cancer,* Alan R. Liss, Inc., 77–96, 1985).

In addition, techniques developed for the production of "chimeric antibodies", the splicing of mouse antibody genes to human antibody genes to obtain a molecule with appropriate antigen specificity and biological activity can be used (Morrison et al., *Proc. Natl. Acad. Sci. USA* 81:6851–6855, 1984; Neubergeretal., *Nature* 312:604–608,1984; Takeda et al., *Nature* 314:452–454, 1985). Alternatively, techniques described for the production of single chain antibodies (U.S. Pat. No. 4,946,778) can be adapted to produce RG1-specific single chain antibodies.

Furthermore, "human" antibodies can be produced using the methods described in U.S. Pat. Nos. 5,877,397 and 5,569,825, which are incorporated herein in full by reference.

Antibodies may also be produced by inducing in vivo production in the lymphocyte population or by screening recombinant immunoglobulin libraries or panels of highly specific binding reagents as disclosed in Orlandi et al. (*Proc. Natl. Acad. Sci. USA* 86:3833–3837, 1989) and Winter and Milstein (*Nature* 349:293–299, 1991).

Antibody fragments which contain specific binding sites for RG1 may also be generated. For example, such fragments include, but are not limited to the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al., *Science* 256:1270–1281, 1989).

The amino acid sequence of RG1 presented herein may be used to select specific regions of the RG1 polypeptide for generating antibodies. As will be understood by those skilled in the art, the regions or epitopes of a RG1 polypeptide to which an antibody is directed may vary with the intended application. For example, antibodies intended for use in an immunoassay for the detection of membrane-bound RG1 on prostate cells should be directed toward accessible epitopes on the RG1 polypeptide. Regions of the RG1 polypeptide that show immunogenic structure, as well as other regions and domains, can readily be identified using various other methods known in the art, such as Chou-Fasman, Garnier-Robson, or Jameson-Wolf analysis. Fragments containing these residues are particularly suited in generating anti-RG1 antibodies. Particularly useful fragments include, but are not limited to, the sequences PLGGESICSAGAPAKYSIT (SEQ ID NO: 8); HSSDYSMWRKNQYVS (SEQ ID NO: 10); DAGTDSGFTFSSPNFATIPQDTV (SEQ ID NO: 11); and NEIVDSASVPET (SEQ ID NO: 12). Generation of polyclonal antibodies to these regions is described in Example 4.

RG1 antibodies of the invention may be particularly useful in diagnostic assays, imaging methodologies, and therapeutic methods for the management of prostate cancer. The invention provides various immunological assays useful for the detection of RG1 polypeptides and for the diagnosis of prostate cancer. Such assays generally comprise one or more RG1 antibodies capable of recognizing and binding a RG1 polypeptide. The most preferred antibodies will selectively bind to RG1 and will not bind (or bind weakly) to non-RG1 polypeptides. The assays include various immunological assay formats well known in the art, including but not limited to various types of radioimmunoassays, enzyme-linked immunoabsorbent assays, and the like. In addition, immunological Imaging methods capable of detecting prostate cancer are also provided by the invention, including but not limited to radioscintigraphic imaging methods using labeled RG1 antibodies. Such assays may be clinically useful in the detection, monitoring and prognosis of prostate cancer.

The above-described antibodies may be employed to isolate or to identify clones expressing the polypeptide or to purify the polypeptide of the present invention by attachment of the antibody to a solid support for isolation and/or purification by affinity chromatography.

Additionally, RG1 antibodies may be used to isolate RG1 positive cells using cell sorting and purification techniques. In particular, RG1 antibodies may be used to isolate prostate cancer cells from xenograft tumor tissue, from cells in culture, etc. using antibody-based cell sorting or affinity purification techniques. Other uses of the RG1 antibodies of the invention include generating anti-idiotypic antibodies that mimic the RG1 polypeptide.

The RG1 antibodies can be used for detecting the presence of prostate cancer or tumor metastasis. The presence of such RG1-containing cells within various biological samples, including serum, prostate and other tissue biopsy specimens, may be detected with RG1 antibodies. In addition, RG1 antibodies may be used in various imaging methodologies such as immunoscintigraphy with Tc-99m (or other isotope) conjugated antibody. For example, an Imaging protocol similar to the one recently described using an In-111 conjugated anti-PSMA antibody may be used to detect recurrent and metastatic prostate carcinomas (Sodee et al., *Clin. Nuc. Med.* 21: 759–766, 1997).

The RG1 antibodies of the invention may be labeled with a detectable marker or conjugated to a second molecule, such as a cytotoxic agent, and used for targeting the second molecule to a RG1 positive cell (Vitetta, E. S. et al., *Immunotoxin Therapy*, in DeVita, Jr, V. T. et al., eds, Cancer: Principles and Practice of Oncology, $4^{th}$ ed., J.B. Lippincott Co., Philadelphia, 2624–2636, 1993). Examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, diptheria toxin, Pseudomonas exotoxin(PE) A, PE40, abrin, and glucocorticoid and other chemotherapeutic agents, as well as radioisotopes. Suitable detectable markers include, but are not limited to, a radioisotope, a fluorescent compound, a bioluminescent compound, chemiluminescent compound, a metal chelator or an enzyme. Suitable radioisotopes include the following: Antimony-124, Antimony-125, Arsenic-74, Barium-103, Barium-140, Beryllium-7, Bismuth-j206, Bismuth-207, Cadmium-109, Cadmium-115m, Calcium-45, Cerium-139, Cerium-141, Cerium-144, Cesium-137, Chromium-51, Cobalt-56, Cobalt-57, Cobalt-58, Cobalt-60, Cobalt-64, Erbium-169, Europium-152, Gadolinium-153, Gold-195, Gold-199, Hafnium-175, Hafnium-181, Indium-11, Iodine-123, Iodine-131, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+ 191, Palladium-103, Platinum-195m, Praseodymium-143, Promethium-147, Protactinium-233, Radium-2226, Rhenium-186, Rubidium-86, Ruthenium-103, Ruthenium-106, Scandium-44, Scandium-46, Selenium-75, Silver-110m, Silver-11, Sodium-22, Strontium-85, Strontium-89, Strontium-90, Sulfur-35, Tantalum-182, Technetium-99m, Tellurium-125, Tellurium-132, Thallium-170, Thallium-204, Thorium-228, Thorium-232, Tin-113, Titanium-44, Tungsten-185, Vanadium-48, Vanadium-49, Ytterbium-169, Yttrium-88, Yttrium-90, Yttrium-91, Zinc-65, and Zirconium-95.

Immunotherapy for Prostate Cancer

The invention provides various immunotherapeutic methods for treating prostate cancer, including antibody therapy, in vivo vaccines, and ex vivo immunotherapy approaches. In one approach, the invention provides RG1 antibodies which may be used systemically to treat prostate cancer. For example, unconjugated RG1 antibodies may be introduced into a patient such that the antibody binds to RG1 on, in or associated with prostate cancer cells and mediates the destruction of the cells, and the tumor, by mechanisms which may include complement-mediated cytolysis, antibody-dependent cellular cytotoxicity, altering the physiologic function of RG1, and/or the inhibition of ligand binding or signal transduction pathways. RG1 antibodies conjugated to toxic agents such as ricin or radioisotopes may also be used therapeutically to deliver the toxic agent directly to RG1-bearing prostate tumor cells and thereby destroy the tumor cells.

Prostate cancer immunotherapy using RG1 antibodies may follow the teachings generated from various approaches which have been successfully employed with respect to other types of cancer, including but not limited to colon cancer (Arlen et al., *Crit. Rev. Immunol.* 18: 133–138, 1998), multiple myeloma (Ozaki et al., *Blood* 90: 3179–3186, 1997; Tsunenari et al., *Blood* 90: 2437–2444, 1997), gastric cancer (Kasprzyk et al, *Cancer Res.* 52: 2771–2776, 1992), B-cell lymphoma (Funakoshi et al., *Immunther. Emphasis Tumor Immunol.* 19: 93–101, 1996), leukemia (Zhong et al., *Leuk. Res.* 20: 581–589, 1996), colorectal cancer (Moun et al., *Cancer Res.* 54 6160–6166, 1994; Velders et al., *Cancer Res.* 55–4398–4403, 1995), and breast cancer (Shepard et al., *J. Clin. Immunol.* 11: 117–127, 1991).

The invention further provides vaccines formulated to contain a RG1 polypeptide or fragment thereof. The use of a tumor antigen in a vaccine for generating humoral and cell-mediated immunity for use in anti-cancer therapy is well known in the art and has been employed in prostate cancer using human PSMA and rodent PAP immunogens (Hodge et al., *Int. J. Cancer* 63: 231–237, 1995; Fong et al., *J. Immunol.* 159: 3113–3117, 1997). Such methods can be readily practiced by employing a RG1 polypeptide, or fragment thereof, or a RG1-encoding nucleic acid molecule and recombinant vectors capable of expressing and appropriately presenting the RG1 immunogen.

For example, viral gene delivery systems may be used to deliver a RG1-encoding nucleic acid molecule. Various viral gene delivery systems which can be used in the practice of this aspect of the invention include, but are not limited to, vaccinia, fowipox, canarypox, adenovirus, influenza, poliovirus, adeno-associated virus, lentivirus, and sindbus virus (Restifo, in *Curr. Opin, Immunol.* 8: 658–663, 1996). Non-viral delivery systems may also be employed by using naked DNA encoding a RG1 polypeptide or fragment thereof introduced into the patient (i.e., intramuscularly) to induce an anti-tumor response In one embodiment, the full-length human rg1 cDNA may be employed. In another embodiment, human rg1 cDNA fragments may be employed. In another embodiment, rg1 nucleic acid molecules encoding specific T lymphocyte (CTL) epitopes may be employed. CTL epitopes can be determined using specific algorithims (e.g., Epimer, Brown University) to identify peptides within a RG1 polypeptide which are capable of optimally binding to specified HLA alleles.

Various ex vivo strategies may also be employed. One approach involves the use of dendritic cells to present a RG1 polypeptide as antigen to a patient's immune system. Dendritic cells express MHC class I and II, B7 costimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., *Prostate* 28: 65–69, 1996; Murphy et al., *Prostate* 29: 371–380, 1996). Dendritic cells can be used to present RG1 polypeptides to T cells in the context of MHC class I and II molecules. In one embodiment, autologous dendritic cells are pulsed with RG1 polypeptides capable of binding to MHC molecules. In another embodiment, dendritic cells are pulsed with the complete RG1 polypeptide. Yet another embodiment involves engineering the overexpression of the rg1 gene in dendritic cells using various implementing vectors known in the art, such as adenovirus (Arthur et al., *Cancer Gene Ther.* 4:17–25,1997), retrovirus (Henderson et al., *Cancer Res.* 56: 3763–3770,1996), lentivirus, adeno-associated virus, DNA transfection (Ribas et al., *Cancer Res.* 57: 2865–2869, 1997), and tumor-derived RNA transfection (Ashley et al., *J. Exp. Med.* 186: 1177–1182, 1997).

Anti-idiotypic anti-RG1 antibodies can also be used in anti-cancer therapy as a vaccine for inducing an immune response to cells expressing a RG1 polypeptide. Specifically, the generation of anti-idiotypic antibodies is well known in the art and can be readily adapted to generate anti-idiotypic anti-RG1 antibodies that mimic an epitope on a RG1 polypeptide (see, for example, Wagner et al., *Hybridoma* 16: 33–40, 1997: Foon et al., *J. Clin. Invest.* 96: 334–342, 1995; Herlyn et al., *Cancer Immunol Immunother* 43: 65–76, 1996) Such an anti-idiotypic antibody can be used in anti-idiotypic therapy as presently practiced with other anti-idiotypic antibodies directed against tumor antigens.

Genetic immunization methods may be employed to generate prophylactic or therapeutic humoral and cellular immune responses directed against cancer cells expressing RG1. Using the RG1-encoding DNA molecules described herein, constructs comprising DNA encoding a RG1 polypeptide/immunogen and appropriate regulatory sequences may be injected directly into muscle or skin of an individual, such that the cells of the muscle or skin take up the construct and express the encoded RG1 polypeptide/immunogen. The RG1 polypeptide/immunogen may be expressed as a cell surface polypeptide or be secreted. Expression of the RG1 polypeptide/immunogen results in the generation of prophylactic or therapeutic humoral and cellular immunity against prostate cancer. Various prophylactic and therapeutic genetic immunization techniques known in the art may be used (for a review, see information and references published at internet address www.genweb.com).

Anti-sense Oligonucleotides, Antisense Vectors, and Ribozymes

Anti-sense polynucleotides complementary to rg1 may be prepared synthetically. Such oligonucleotides may be delivered into cells with or without lipids that may assist uptake of the anti-sense oligonucleotides into cells.

Alternatively, expression vectors derived from retroviruses, adenovirus, herpes or vaccinia viruses, or from various bacterial plasmids, may also be used for construction and delivery of recombinant vectors which will express anti-sense rg1. See, for example, the techniques described in Sambrook et al. (supra) and Ausubel et al. (supra).

The polynucleotides comprising the full length cDNA sequence and/or its regulatory elements enable researchers to use rg1 polynucleotides as an investigative tool in sense strands (Youssoufian and Lodish, *Mol. Cell. Biol.* 13:98–104,1993) or antisense strands (Eguchi, et al., *Annu. Rev. Biochem.* 60:631–652, 1991) for the regulation of gene function. Such technology is now well known in the art, and sense or antisense oligomers, or larger fragments, can be designed from various locations along the coding or control regions.

Genes encoding RG1 can be turned off by transfecting a cell or tissue with expression vectors which express high levels of a desired rg1 polynucleotide fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modification of gene expression can be obtained by designing antisense molecules, DNA or RNA, to control regions of rg1, i.e., the promoters, enhancers, and introns. Oligonucleotides derived from the transcription initiation site, e.g. between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee, J. E. et al. (In Huber and Car, *Molecular and Immunologic Approaches*, Futura Publishing Co., Mt. Kisco, N.Y., 1994).

Ribozymes are enzymatic RNA molecules capable of catalyzing the specific cleavage of RNA (U.S. Pat. No. 4,987,071; WO 93/23057). The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of RNA encoding RG1. Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays (Irie et al., *Advance. Pharmacol.* 40:207–257, 1997).

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription or by DNA sequences encoding RG1. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecules or the use of phosphorothioate or 2' O-methyl rather than phosphodiesterase linkages within the backbone of the molecule. Increased stability can also be achieved by the inclusion of nontraditional bases such as inosine and queosine as well as acetyl-, methyl-, thio- and similarly modified forms of adenine, cytidine, guanine, thymine, and uridine which are not as easily recognized by endogenous endonucleases.

Methods for introducing antisense vectors into cells or tissues include those methods discussed infra and which are equally suitable for in vivo, in vitro and ex vivo therapy. For ex vivo therapy, antisense vectors are introduced into cells taken from the patient and clonally propagated for autologous transplant back into that same patient as presented in U.S. Pat. Nos. 5,399,493 and 5,437,994, disclosed herein by reference. Delivery by transfection and by liposome or other lipid based or non-lipid based agents are well known in the art.

Assays for Identifying Agents Binding to RG1

The present invention also relates to assays and methods which can be used to identify agents that bind to RG1. Specifically, agents that bind to RG1 can be identified by the ability of the RG1 ligand or other agent or constituent to bind to RG1 and/or the ability to inhibit/stimulate RG1 activity.

Alternatively, agents that bind to a RG1 polypeptide can be identified using a yeast two-hybrid system or a binding capture assay. In the yeast two hybrid system, an expression unit encoding a fusion protein made up of one subunit of a two subunit transcription factor and the RG1 polypeptide is introduced and expressed in a yeast cell. The cell is further modified to contain (1) an expression unit encoding a detectable marker whose expression requires the two subunit transcription factor for expression and (2) an expression unit that encodes a fusion protein made up of the second subunit of the transcription factor and a cloned segment of DNA. If the cloned segment of DNA encodes a protein that binds to the RG1 polypeptide, the expression results in the interaction of RG1 and the encoded protein. This brings the two subunits of the transcription factor into binding proximity, allowing reconstitution of the transcription factor. This results in expression of the detectable marker. The yeast two hybrid system is particularly useful in screening a library of cDNA encoding segments for cellular binding partners of RG1.

RG1 polypeptides which may be used in the above assays include, but are not limited to, an isolated RG1 polypeptide, a fragment of a RG1 polypeptide, a cell that has been altered to express a RG1 polypeptide, or a fraction of a cell that has been altered to express a RG1 polypeptide. Further, the RG1 polypeptide can be the entire polypeptide or a defined fragment of the RG1 polypeptide. It will be apparent to one of ordinary skill in the art that so long as the RG1 polypeptide can be assayed for agent binding, e.g. by a shift in molecular weight or activity, the present assay can be used.

The method used to identify whether an agent/cellular component binds to a RG1 polypeptide will be based primarily on the nature of the RG1 polypeptide used. For example, a gel retardation assay can be used to determine whether an agent binds to RG1 or a fragment thereof. Alternatively, immunodetection and biochip technologies can be adopted for use with the RG1 polypeptide. A skilled artisan can readily employ numerous art-known techniques for determining whether a particular agent binds to an RG1 polypeptide.

Agents and cellular components can be further tested for the ability to modulate the activity of an RG1 polypeptide using a cell-free assay system or a cellular assay system. As the activities of the RG1 polypeptide become more defined, functional assays based on the identified activity can be employed.

As used herein, an agent is said to antagonize RG1 activity when the agent reduces RG1 activity. The preferred antagonist will selectively antagonize RG1, not affecting any other cellular proteins. Further, the preferred antagonist will reduce RG1 activity by more than 50%, more preferably by more than 90%, most preferably eliminating all RG1 activity.

Agents that are assayed in the above method can be randomly selected or rationally selected or designed. As used herein, an agent is said to be randomly selected when the agent is chosen randomly without considering the specific sequences of the RG1 polypeptide. An example of randomly selected agents is the use of a chemical library or a peptide combinatorial library, or growth broth of an organism or plant extract.

As used herein, an agent is said to be rationally selected or designed when the agent is chosen on a nonrandom basis that takes into account the sequence of the target site an/or its conformation in connection with the agent's action. Agents can be rationally selected or rationally designed by utilizing the peptide sequences that make up the RG1 polypeptide. For example, a rationally selected peptide agent can be a peptide whose amino acid sequence is identical to a fragment of an RG1 polypeptide.

The agents tested in the methods of the present invention can be, as examples, peptides, antibodies, oligonucleotides, small molecules and vitamin derivatives, as well as carbohydrates. A skilled artisan can readily recognize that there is no limit as to the structural nature of the agents used in the present screening method. One class of agents of the present invention are peptide agents whose amino acid sequences are chosen based on the amino acid sequence of the RG1 polypeptide.

Peptide agents can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if no-gene-encoded amino acids are to be included.

Another class of agent of the present invention are antibodies immunoreactive with critical positions of the RG1 polypeptide. As described above, antibodies are obtained by immunization of suitable mammalian subjects with peptides, containing as antigenic regions, those portions of the RG1 polypeptide intended to be targeted by the antibodies. Such agents can be used in competitive binding studies to identify second generation inhibitory agents as well as to block RG1 activity.

The cellular extracts tested in the methods of the present invention can be, as examples, aqueous extracts of cells or tissues, organic extracts of cells or tissues or partially purified cellular fractions A skilled artisan can readily recognize that there is no limit as to the source of the cellular extract used in the screening method of the present invention.

Agents that bind a RG1 polypeptide, such as a RG1 antibody, can be used to modulate the activity of RG1,to target anticancer agents to appropriate mammalian cells, or to identify agents that block the interaction with RG1. Cells expressing RG1 can be targeted or identified by using an agent that binds to RG1.

How the RG1 binding agents will be used depends on the nature of the RG1 binding agent. For example, a RG1 binding agent can be used to: deliver conjugated toxins, such as diphtheria toxin, cholera toxin, ricin or pseudomonas exotoxin, to a RG1 expressing cell; modulate RG1 activity; to directly kill a RG1 expressing cell; or in screens to identify competitive binding agents. For example, a RG1 inhibitory agent can be used to directly inhibit the growth of RG1 expressing cells whereas a RG1 binding agent can be used as a diagnostic agent.

Pharmaceutical Compositions and Administration

The present invention also relates to pharmaceutical compositions which may comprise rg1 polynucleotides, RG1 polypeptides, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

The present invention also relates to the administration of pharmaceutical compositions. Such administration is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxilliaries which facilitate processing of the active compounds into preparations which can be used pharmaceutically Further details on techniques for formulation and administration may be found in the latest edition of Remington's Pharmaceutical Sciences (Ed. Maack Publishing Co, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxilliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl, cellulose, hydroxypropylmethylcellulose, or sodium carboxymethylcellulose; and gums including arabic and tragacanth; and proteins such as gelatin and collagen. If desired, disintegrating or solubilizing agents may be added, such as the crosslinked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol and/or titanium dioxide, lacquer solutions, and suitable organic solvents or solvent mixtures. Dyestuffs or pigments may be added to the tablets or dragee coatings for product identification or to characterize the quantity of active compound, ie dosage.

Pharmaceutical preparations that can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture use or sale of pharmaceuticals or biological products, reflecting approval by the agency of the manufacture, use or sale of the product for human administration.

Manufacture and Storage.

The pharmaceutical compositions of the present invention may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a salt and can be formed with may acids, including by not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%–2% sucrose, 2%–7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of RG1, such labeling would include amount, frequency and method of administration.

Therapeutically Effective Dose.

Pharmaceutical compositions suitable for use in the present invention include compositions wherein the active ingredients are contained in an effective amount to achieve the intended purpose, i.e. treatment of a particular disease state characterized by RG1 expression. The determination of an effective dose is well within the capability of those skilled in the art.

For any compound, the therapeutically effective dose can be estimated initially either in cell culture assays, e.g., neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions which exhibit large therapeutic indices are preferred. The data obtained from cell culture assays and animal studies is used in formulating a range of dosage for human use. The dosage of such compounds lies preferably within a range of circulating concentrations what include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for polynucleotides than for proteins or their inhibitors. Similarly, delivery of polynucleotides or polypeptides will be specific to particular cells, conditions, locations, etc.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as Sambrook et al., *Molecular Cloning: A Laboratory Manual,* 2nd Ed; Cold Spring Harbor Laboratory Press, Cold Spring Harbor, N.Y., 1989.

EXAMPLE 1

Identification of Human rg1 Polynucleotide

Rg1 was identified as a gene expressed in the prostate by mining Incyte's LifeSeq database. The nucleotide sequence was identified by an annotation serch of the database, using the "Protein Function" tool provided by Incyte for the purpose of searching the database. The nucleotide sequence was found in the category of cell adhesion molecules in the annotated database and was described as a homologue of f-spondin. Electronic Northern analysis of the distribution of rg1 polynucleotide sequences in the set of libraries in the database revealed that rg1 was expressed at high levels in the prostate libraries and at lower levels in a number of other tissue libraries, including those from normal and tumor tissues.

Following assembly of the set of rg1 clones in the database into a contiguous polynucleotide sequence, and editing of the contiguous sequence, a full-length coding sequence was identified in the predicted assembled polynucleotide. This sequence coded for a protein homologous to f-spondin and to Mindin-2.

Incyte clones 1640796, 1712252, and 1880265 were obtained from Incyte for experimental work and clone 3360733 was identified as containing the most 5' nucleotide sequence. This clone was fully sequenced and contained the full coding sequence for the predicted RG1 protein. This sequence is shown in FIG. 1 (SEQ D NO: 1).

EXAMPLE 2

Rg1 mRNA Expression

The expression of rg1 mRNA in a variety of samples from normal and tumor tissues and in cell lines, was determined by semi-quantitative PCR using a Taqman assay, (Perkin-Elmer). Prostate normal, benign and tumor tissue samples that had been graded according to a modified Gleason grading system were obtained from the Urology Department at Stanford University School of Medicine. RNA was isolated from these by standard procedures. RNA from other tumor and normal tissues was purchased from commercial sources, including Clonetech, and Biochain. Prostate tumor cell lines, (PC-3, LNCaP and DU145), were obtained from American Type Culture Collection and propagated in culture by standard methods using serum containing medium. Xenograft tumors derived from these cell lines were established in nude mice and harvested from the mice approximately 4–6 weeks after implantation. RNA was isolated from the tumors by standard procedures.

Taqman based PCR analysis was performed using the primers CGC GCA TAG CTC CGA CTA C (SEQ ID NO: 3) and GCC GCG TCC GCA AAG (SEQ ID NO: 4) and the Taqman probe: 6-FAM-AGG AAG AAC CAG TAC GTC AGT AAC GGG CTG-Tamra (SEQ ID NO: 5).

These primers and probe were designed using Perkin Elmer's Primer Express software and were synthesized by Synthetic Genetics. PCR reactions were carried out for 30–40 cycles and quantified using prostate RNA to generate a standard curve for relative comparison. This analysis demonstrated that rg1 mRNA was detected at highest abundance in the prostate and at significantly lower levels in several other tissues (See FIG. 5).

EXAMPLE 3

Cloning and Expression of RG1 in BHK Cells

The RG1 coding region was obtained from Incyte plasmid 3360733. The coding sequence was PCR amplified with primers SST115 (5'-TCCCTCTAGAGCCACCATGGAAAAC-CCCAGCCCGGC -3') (SEQ ID NO: 6) and SST113 (5'-AAGGCATCACGTGTTAGACGCAGTTATCAGGGAC G-3') (SEQ ID NO: 7) in a standard PCR reaction (100 ul) using 1×Pfu Turbo polymerase buffer (Stratagene, La Jolla, Calif.)/200 uM dNTPs/0.2 uM oligonucleotide primers/2.5 U Pfu Turbo polymerase (Stratagene). PCR amplification conditions were as follows: 3 mins at 95° C., (15 seconds at 95° C., 30 seconds at 60° C., 2 minutes at 72° C.)×35, 72° C. for 7 minutes. The resulting PCR amplified product was purified using a QIAquick PCR column (Qiagen, Valencia, Calif.) and digested with XbaI and PmlI restriction enzymes to result in a 1010 bp fragment that was purified from a 1% agarose gel using a BIO 101 GeneClean Kit (Vista, Calif.). The purified fragment was ligated (using Epicientre Fast Link Kit, (Epicenter, Madison, Wis.) to the noncytopathic Sindbis expression vector pSINrep21(Agapov et al, 1998, PNAS 95: 12989–12994) digested with XbaI and PmlI, and transformed into DH5 alpha competent cells (Life Technologies, Gaithersburg, Calif.) and selected on LB agar plates containing ampicillin (100 ug/ml). One such ampicillin resistant colony was grown in LB medium with ampicillin and shown by sequence analysis to contain the inserted RG1 coding sequence. This plasmid was called pPEG6.

Two micrograms of pPEG6 was used to transfect 1-3×10$^5$ bovine hamster kidney cells (BHK) cells using Lipofectamine Plus reagent (Life Technologies, Gaithersburg, Md.) according to the manufacturer's instructions. Following transfection, cells were incubated in DMEM plus fetal blood serum for 24–48 hours, at which time the cells were split 1 to 10 and selection for the plasmid containing cells was initiated by adding puromycin (2.5 ug/ml final concentration) and DMEM containing serum. After the cells were confluent (4–5 days post puromycin addition) the cells were washed with PBS, split 1 to 10, and DMEM medium with serum and 5 ug/ml puromycin was added. After an additional 2–3 days, the medium was replaced with DMEM and 5 ug/ml puromycin without serum, grown for 2–3 days and the presence of RG1 protein was detected in the medium by Western analysis using RG1 antibodies. RG1 protein was detected at a level of 1 ug/ml.

EXAMPLE 4

Antibody Generation

Rabbit polyclonal antisera were raised against five synthetic polypeptide sequences derived from the RG1 protein sequence. These sequences were selected because of their predicted positions at the surface of the protein, in order to generate antisera that are more likely to recognize surface epitopes. Cysteine residues were replaced with aminobutyric acid (Abu) to aid synthesis. The specific amino acid sequences, positions on the RG1 protein and designations for the five peptides are listed below.

| Designation | Position | Amino Acid Sequence |
| --- | --- | --- |
| 1C | 28–46 | PLGGESICSAGAPAKYSIT (SEQ ID NO: 8) |
| 2C | 46–64 | TFTGKWSQTAFPKQYPLFR (SEQ ID NO: 9) |
| 3C | 77–91 | HSSDYSMWRKNQYVS (SEQ ID NO: 10) |
| 4C | 188–210 | DAGTDSGFTFSSPNFATIPQDTV (SEQ ID NO: 11) |
| 5C | 263–274 | NEIVDSASVPET (SEQ ID NO: 12) |

Peptides were covalently coupled to keyhole limpet hemocyanin (KLH), via an additional carboxyl-terminal cysteine, for use as an immunogen. Similarly, a bovine serum albumin (BSA) conjugate was prepared for the analysis of antisera titers via ELISA.

Two animals were immunized with each peptide. Initial immunizations were performed in Freunds complete adjuvant (0.5 mg/animal), followed by boosts at three week intervals with 0.25 mg/animal in Freunds incomplete adjuvant applied intramuscularly. Periodic test bleeds were taken and antibody titers against the specific BSA-peptide conjugate were measured by ELISA and compared with preimmune sera Antisera against peptides 1C and 3C were shown to be active. Antisera against peptide 2C did not recognize RG1 polypeptide. Antisera against peptides 4C and 5C were not tested.

Human monoclonal antibodies against RG1 were generated by immunizing transgenic mice against RG1 peptides and a 6-histidine-tagged RG1 fusion protein expressed in *E. coli*. Splenocytes of these animals were fused with myeloma cells to produce hybridoma cells. The resulting hybridomas were screened by ELISA for those producing antibodies directed against RG1 peptides and protein.

EXAMPLE 5

Western Blot Analysis of Antibodies

Antisera were tested for RG1 specificity via Western blotting. RG1 specific antisera (those raised against sequences 1C and 3C, above) were tested on RG1 transiently expressed in COS cells, native RG1 secreted from LNCaP cells and RG1 produced from transfected baby hamster kidney cells (BHK). RG1-specific antisera were further tested on lysates prepared from: LNCaP tumors, LNCaP cells, PC3 tumors, PC3 cells and several clinical samples of human prostate tumors. Cells and tissues were lysed in detergent buffer. After boiling for 5 min, 10 ul of each lysate was loaded onto a 12% SDS-polyacrylamide gel to resolve proteins. Separated proteins were then transferred to nitrocellulose membranes. Binding specificity of RG1 antibodies was verified by binding in the presence of the homologous and heterologous peptides. RG1-specific antisera could detect the protein in all samples but PC-3 cells and PC-3 tumors.

EXAMPLE 6

Purification of Native RG1 Protein Secreted from LNCaP Cells

LNCaP cells grown in culture were shown to secrete native RG1 protein by Western blot analysis. In order to purify the native protein, cells were grown for 48 hours in media lacking serum This serum-free conditioned media was harvested, centrifuged to remove any cells, and concentrated approximately fifty-fold by ultrafiltration. The concentrated media was then diluted ten-fold with 20 mM sodium acetate buffer, pH 6.5 and loaded onto a Q-Sepharose anion exchange column. Column elution consisted of a sodium chloride gradient (0.5% per minute) while collecting 2.0 ml fractions. The RG1 protein eluted at approximately 75 mM NaCl as determined by Western blot and SDS PAGE. The native RG1 protein runs at a slightly lower molecular weight than the 6 histidine-RG1 fusion protein expressed in bacteria, presumably because it lacks the fusion peptide.

EXAMPLE 7

Immunohistochemical Staining of RG1 Expression

The expression of RG1 protein was determined by LifeSpan Biosciences, Inc. in a variety of human tissues, including kidney, lung, pancreas, muscle, brain and prostate. Additional prostate tissues were obtained from the Urology Department at Stanford University School of Stanford and tested at Berlex The tissue sections were deparaffinized using standard procedures. The polyclonal antibody RG1–3C was used as a primary antibody and the detection system consisted of using Vector ABC-AP kit (AK5002) with a Vector red substrate kit (Sk5002). As a negative control, the staining was carried out in the absence of the primary antibody.

All publications and patents mentioned in the above specification are herein incorporated by reference. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto

What is claimed is:

1. A method for detecting metastasis of prostate cancer in a subject, wherein the method comprises:
   (a) obtaining from the subject a non-prostate tissue and/or fluid sample;
   (b) contacting the sample with an antibody or antibody fragment which specifically binds to one or more epitopes present in a human RG1 polypeptide having the amino acid sequence of SEQ ID NO: 2;
   (c) detecting the binding of the antibody or antibody fragment with the human RG1 polypeptide in the sample; and
   (d) determining if the level of binding in the subject is increased over the level detected in normal controls.

2. The method of claim 1, wherein the antibody or antibody fragment is labeled with a compound selected from the group consisting of a radiolabel, a chromophore and a fluorescer, so as to directly or indirectly produce a detectable signal.

3. The method of claim 1, wherein the antibody fragment is a F(ab')2 fragment.

4. The antibody of claim 1, wherein the antibody or antibody fragment specifically binds to the amino acid sequence PLGGESICSAGAPAKYSIT (SEQ ID NO: 8).

5. The antibody of claim 1, wherein the antibody or antibody fragment specifically binds to the amino acid sequence HSSDYSMWRKNQYVS (SE ID NO: 10).

6. The antibody of claim 1, wherein the antibody or antibody fragment specifically binds to the amino acid sequence DAGTDSGFTFSSPNFATIPQDTV (SEQ IDNO: 11).

7. The antibody of claim 1, wherein the antibody or antibody fragment specifically binds to the amino acid sequence NEIVDSASVPET (SEQ ID NO:12).

8. The antibody of claim 1, wherein the antibody is a polyclonal antibody.

9. The antibody of claim 1, wherein the antibody is a monoclonal antibody.

10. A method of detecting metastasis of prostate cancer in a subject, wherein the method comprises:
   (a) injecting the subject with an appropriate dose of a radiolabeled antibody or antibody-fragment which specifically binds to one or more epitopes present in a human RG1 polypeptide having the amino acid sequence of SEQ ID NO: 2;
   (b) detecting by immunoscintography the binding of the radiolabeled antibody or antibody fragment to one or more epitopes present in the human RG1 polypeptide within the subject; and (c) determining if the level of binding in the subject is increased over the level detected in normal controls.

11. The method of claim 10, wherein the radiolabel is In-111 or tc-99m.

* * * * *

UNITED STATES PATENT AND TRADEMARK OFFICE
CERTIFICATE OF CORRECTION

PATENT NO. : 6,682,902 B2
APPLICATION NO. : 09/732357
DATED : January 27, 2004
INVENTOR(S) : Richard Harkins et al.

It is certified that error appears in the above-identified patent and that said Letters Patent is hereby corrected as shown below:

In column 49, line 65, claim 4 recites in the preamble "The antibody of claim 1", but should read --The method of claim 1--.

In column 50, line 44, claim 5 recites in the preamble "The antibody of claim 1", but should read --The method of claim 1--.

In column 50, line 47, claim 6 recites in the preamble "The antibody of claim 1", but should read --The method of claim 1--.

In column 50, line 51, claim 7 recites in the preamble "The antibody of claim 1", but should read --The method of claim 1--.

In column 50, line 54, claim 8 recites in the preamble "The antibody of claim 1", but should read --The method of claim 1--.

In column 50, line 56, claim 9 recites in the preamble "The antibody of claim 1", but should read --The method of claim 1--.

Signed and Sealed this

Fifth Day of May, 2009

JOHN DOLL
*Acting Director of the United States Patent and Trademark Office*

SEQUENCE LISTING

```
<160> NUMBER OF SEQ ID NOS: 13

<210> SEQ ID NO 1
<211> LENGTH: 1785
<212> TYPE: DNA
<213> ORGANISM: Homo sapiens
<220> FEATURE:
<221> NAME/KEY: CDS
<222> LOCATION: (296)..(1291)
<223> OTHER INFORMATION:

<400> SEQUENCE: 1
agaaaggggt gcggcagcac tgccagggga agagggtgat ccgacccggg gaaggtcgct     60
gggcagggcg agttgggaaa gcggcagccc ccgccgcccc cgcagcccct tctcctcctt    120
tctcccacgt cctatctgcc tctcgctgga ggccaggccg tgcagcatcg aagacaggag    180
gaactggagc ctcattggcc ggcccggggc gccggcctcg ggcttaaata ggagctccgg    240
gctctggctg ggacccgacc gctgccggcc gcgctcccgc tgctcctgcc gggtg atg     298
                                                             Met
                                                             1
```

```
                                                         -continued gaa aac ccc agc ccg gcc gcc gcc ctg ggc aag gcc ctc tgc gct ctc        346
Glu Asn Pro Ser Pro Ala Ala Ala Leu Gly Lys Ala Leu Cys Ala Leu
         5                   10                  15 ctc ctg gcc act ctc ggc gcc gcc ggc cag cct ctt ggg gga gag tcc        394
Leu Leu Ala Thr Leu Gly Ala Ala Gly Gln Pro Leu Gly Gly Glu Ser
         20                  25                  30 atc tgt tcc gcc gga gcc ccg gcc aaa tac agc atc acc ttc acg ggc        442
Ile Cys Ser Ala Gly Ala Pro Ala Lys Tyr Ser Ile Thr Phe Thr Gly
         35                  40                  45 aag tgg agc cag acg gcc ttc ccc aag cag tac ccc ctg ttc cgc ccc        490
Lys Trp Ser Gln Thr Ala Phe Pro Lys Gln Tyr Pro Leu Phe Arg Pro
50                  55                  60                  65 cct gcg cag tgg tct tcg ctg ctg ggg gcc gcg cat agc tcc gac tac        538
Pro Ala Gln Trp Ser Ser Leu Leu Gly Ala Ala His Ser Ser Asp Tyr
             70                  75                  80 agc atg tgg agg aag aac cag tac gtc agt aac ggg ctg cgc gac ttt        586
Ser Met Trp Arg Lys Asn Gln Tyr Val Ser Asn Gly Leu Arg Asp Phe
         85                  90                  95 gcg gag cgc ggc gag gcc tgg gcg ctg atg aag gag atc gag gcg gcg        634
Ala Glu Arg Gly Glu Ala Trp Ala Leu Met Lys Glu Ile Glu Ala Ala
         100                 105                 110 ggg gag gcg ctg cag agc gtg cac gcg gtg ttt tcg gcg ccc gcc gtc        682
Gly Glu Ala Leu Gln Ser Val His Ala Val Phe Ser Ala Pro Ala Val
         115                 120                 125 ccc agc ggc acc ggg cag acg tcg gcg gag ctg gag gtg cag cgc agg        730
Pro Ser Gly Thr Gly Gln Thr Ser Ala Glu Leu Glu Val Gln Arg Arg
130                 135                 140                 145 cac tcg ctg gtc tcg ttt gtg gtg cgc atc gtg ccc agc ccc gac tgg        778
His Ser Leu Val Ser Phe Val Val Arg Ile Val Pro Ser Pro Asp Trp
             150                 155                 160 ttc gtg ggc gtg gac agc ctg gac ctg tgc gac ggg gac cgt tgg cgg        826
Phe Val Gly Val Asp Ser Leu Asp Leu Cys Asp Gly Asp Arg Trp Arg
         165                 170                 175 gaa cag gcg gcg ctg gac ctg tac ccc tac gac gcc ggg acg gac agc        874
Glu Gln Ala Ala Leu Asp Leu Tyr Pro Tyr Asp Ala Gly Thr Asp Ser
         180                 185                 190 ggc ttc acc ttc tcc tcc ccc aac ttc gcc acc atc ccg cag gac acg        922
Gly Phe Thr Phe Ser Ser Pro Asn Phe Ala Thr Ile Pro Gln Asp Thr
         195                 200                 205 gtg acc gag ata acg tcc tcc tct ccc agc cac ccg gcc aac tcc ttc        970
Val Thr Glu Ile Thr Ser Ser Ser Pro Ser His Pro Ala Asn Ser Phe
210                 215                 220                 225 tac tac cca cgg ctg aag gcc ctg cct ccc atc gcc agg gtg aca ctg       1018
Tyr Tyr Pro Arg Leu Lys Ala Leu Pro Pro Ile Ala Arg Val Thr Leu
             230                 235                 240 gtg cgg ctg cga cag agc ccc agg gcc ttc atc cct ccc gcc cca gtc       1066
Val Arg Leu Arg Gln Ser Pro Arg Ala Phe Ile Pro Pro Ala Pro Val
         245                 250                 255 ctg ccc agc agg gac aat gag att gta gac agc gcc tca gtt cca gaa       1114
Leu Pro Ser Arg Asp Asn Glu Ile Val Asp Ser Ala Ser Val Pro Glu
         260                 265                 270 acg ccg ctg gac tgc gag gtc tcc ctg tgg tcg tcc tgg gga ctg tgc       1162
Thr Pro Leu Asp Cys Glu Val Ser Leu Trp Ser Ser Trp Gly Leu Cys
         275                 280                 285 gga ggc cac tgt ggg agg ctc ggg acc aag agc agg act cgc tac gtc       1210
Gly Gly His Cys Gly Arg Leu Gly Thr Lys Ser Arg Thr Arg Tyr Val
290                 295                 300                 305 cgg gtc cag ccc gcc aac aac ggg agc ccc tgc ccc gag ctc gaa gaa       1258
Arg Val Gln Pro Ala Asn Asn Gly Ser Pro Cys Pro Glu Leu Glu Glu
         310                 315                 320
```

-continued

```
gag gct gag tgc gtc cct gat aac tgc gtc taa gaccagagcc ccgcagcccc   1311
Glu Ala Glu Cys Val Pro Asp Asn Cys Val
            325                 330 tggggccccc cggagccatg gggtgtcggg ggctcctgtg caggctcatg ctgcaggcgg   1371
ccgagggcac aggggtttc gcgctgctcc tgaccgcggt gaggccgcgc cgaccatctc   1431
tgcactgaag ggccctctgg tggccggcac gggcattggg aaacagcctc ctcctttccc   1491
aaccttgctt cttaggggcc cccgtgtccc gtctgctctc agcctcctcc tcctgcagga   1551
taaagtcatc cccaaggctc cagctactct aaattatgtc tccttataag ttattgctgc   1611
tccaggagat tgtccttcat cgtccagggg cctggctccc acgtggttgc agatacctca   1671
gacctggtgc tctaggctgt gctgagccca ctctcccgag ggcgcatcca agcgggggcc   1731
acttgagaag tgaataaatg gggcggtttc ggaagcgtca aaaaaaaaaa aaaa          1785
```

<210> SEQ ID NO 2
<211> LENGTH: 331
<212> TYPE: PRT
<213> ORGANISM: Homo sapiens

<400> SEQUENCE: 2

```
Met Glu Asn Pro Ser Pro Ala Ala Leu Gly Lys Ala Leu Cys Ala
1               5                   10                  15

Leu Leu Leu Ala Thr Leu Gly Ala Ala Gly Gln Pro Leu Gly Gly Glu
                20                  25                  30

Ser Ile Cys Ser Ala Gly Ala Pro Ala Lys Tyr Ser Ile Thr Phe Thr
            35                  40                  45

Gly Lys Trp Ser Gln Thr Ala Phe Pro Lys Gln Tyr Pro Leu Phe Arg
    50                  55                  60

Pro Pro Ala Gln Trp Ser Ser Leu Leu Gly Ala Ala His Ser Ser Asp
65                  70                  75                  80

Tyr Ser Met Trp Arg Lys Asn Gln Tyr Val Ser Asn Gly Leu Arg Asp
                85                  90                  95

Phe Ala Glu Arg Gly Glu Ala Trp Ala Leu Met Lys Glu Ile Glu Ala
                100                 105                 110

Ala Gly Glu Ala Leu Gln Ser Val His Ala Val Phe Ser Ala Pro Ala
            115                 120                 125

Val Pro Ser Gly Thr Gly Gln Thr Ser Ala Glu Leu Glu Val Gln Arg
    130                 135                 140

Arg His Ser Leu Val Ser Phe Val Val Arg Ile Val Pro Ser Pro Asp
145                 150                 155                 160

Trp Phe Val Gly Val Asp Ser Leu Asp Leu Cys Asp Gly Asp Arg Trp
                165                 170                 175

Arg Glu Gln Ala Ala Leu Asp Leu Tyr Pro Tyr Asp Ala Gly Thr Asp
                180                 185                 190

Ser Gly Phe Thr Phe Ser Ser Pro Asn Phe Ala Thr Ile Pro Gln Asp
            195                 200                 205

Thr Val Thr Glu Ile Thr Ser Ser Pro Ser His Pro Ala Asn Ser
    210                 215                 220

Phe Tyr Tyr Pro Arg Leu Lys Ala Leu Pro Pro Ile Ala Arg Val Thr
225                 230                 235                 240

Leu Val Arg Leu Arg Gln Ser Pro Arg Ala Phe Ile Pro Pro Ala Pro
                245                 250                 255

Val Leu Pro Ser Arg Asp Asn Glu Ile Val Asp Ser Ala Ser Val Pro
                260                 265                 270
```

```
Glu Thr Pro Leu Asp Cys Glu Val Ser Leu Trp Ser Trp Gly Leu
            275                 280                 285

Cys Gly Gly His Cys Gly Arg Leu Gly Thr Lys Ser Arg Thr Arg Tyr
        290                 295                 300

Val Arg Val Gln Pro Ala Asn Asn Gly Ser Pro Cys Pro Glu Leu Glu
305                 310                 315                 320

Glu Glu Ala Glu Cys Val Pro Asp Asn Cys Val
                325                 330

<210> SEQ ID NO 3
<211> LENGTH: 19
<212> TYPE: DNA
<213> ORGANISM: artificial sequence
<220> FEATURE:
<223> OTHER INFORMATION: primer

<400> SEQUENCE: 3
cgcgcatagc tccgactac                                            19

<210> SEQ ID NO 4
<211> LENGTH: 15
<212> TYPE: DNA
<213> ORGANISM: artificial sequence
<220> FEATURE:
<223> OTHER INFORMATION: primer

<400> SEQUENCE: 4
gccgcgtccg caaag                                                15

<210> SEQ ID NO 5
<211> LENGTH: 30
<212> TYPE: DNA
<213> ORGANISM: artificial sequence
<220> FEATURE:
<223> OTHER INFORMATION: probe

<400> SEQUENCE: 5
aggaagaacc agtacgtcag taacgggctg                                30

<210> SEQ ID NO 6
<211> LENGTH: 36
<212> TYPE: DNA
<213> ORGANISM: artificial sequence
<220> FEATURE:
<223> OTHER INFORMATION: primer

<400> SEQUENCE: 6
tccctctaga gccaccatgg aaaacccag cccggc                          36

<210> SEQ ID NO 7
<211> LENGTH: 35
<212> TYPE: DNA
<213> ORGANISM: artificial sequence
<220> FEATURE:
<223> OTHER INFORMATION: primer2

<400> SEQUENCE: 7
aaggcatcac gtgttagacg cagttatcag ggacg                          35

<210> SEQ ID NO 8
<211> LENGTH: 19
<212> TYPE: PRT
<213> ORGANISM: Homo sapiens
```

```
<400> SEQUENCE: 8

Pro Leu Gly Gly Glu Ser Ile Cys Ser Ala Gly Ala Pro Ala Lys Tyr
 1               5                  10                  15

Ser Ile Thr

<210> SEQ ID NO 9
<211> LENGTH: 19
<212> TYPE: PRT
<213> ORGANISM: Homo sapiens

<400> SEQUENCE: 9

Thr Phe Thr Gly Lys Trp Ser Gln Thr Ala Phe Pro Lys Gln Tyr Pro
 1               5                  10                  15

Leu Phe Arg

<210> SEQ ID NO 10
<211> LENGTH: 15
<212> TYPE: PRT
<213> ORGANISM: Homo sapiens

<400> SEQUENCE: 10

His Ser Ser Asp Tyr Ser Met Trp Arg Lys Asn Gln Tyr Val Ser
 1               5                  10                  15

<210> SEQ ID NO 11
<211> LENGTH: 23
<212> TYPE: PRT
<213> ORGANISM: Homo sapiens

<400> SEQUENCE: 11

Asp Ala Gly Thr Asp Ser Gly Phe Thr Phe Ser Ser Pro His Phe Ala
 1               5                  10                  15

Thr Ile Pro Gln Asp Thr Val
                20

<210> SEQ ID NO 12
<211> LENGTH: 12
<212> TYPE: PRT
<213> ORGANISM: Homo sapiens

<400> SEQUENCE: 12

Asn Glu Ile Val Asp Ser Ala Ser Val Pro Glu Thr
 1               5                  10

<210> SEQ ID NO 13
<211> LENGTH: 330
<212> TYPE: PRT
<213> ORGANISM: Rattus norvegicus

<400> SEQUENCE: 13

Met Glu Asn Val Ser Phe Ser Leu Asp Arg Thr Leu Trp Val Phe Leu
 1               5                  10                  15

Leu Ala Met Leu Gly Ser Thr Ala Gly Gln Pro Leu Gly Gly Glu Ser
                20                  25                  30

Val Cys Thr Ala Arg Pro Leu Ala Arg Tyr Ser Ile Thr Phe Thr Gly
            35                  40                  45

Lys Trp Ser Gln Thr Ala Phe Pro Lys Gln Tyr Pro Leu Phe Arg Pro
        50                  55                  60

Pro Ala Gln Trp Ser Ser Leu Leu Gly Ala Ala His Ser Ser Asp Tyr
 65                 70                  75                  80
```

```
                                        -continued

Ser Met Trp Arg Lys Asn Glu Tyr Val Ser Asn Gly Leu Arg Asp Phe
             85                  90                  95

Ala Glu Arg Gly Glu Ala Trp Ala Leu Met Lys Glu Ile Glu Ala Ala
            100             105                 110

Gly Glu Lys Leu Gln Ser Val His Ala Val Phe Ser Ala Pro Ala Val
            115             120                 125

Pro Ser Gly Thr Gly Gln Thr Ser Ala Glu Leu Glu Val His Pro Arg
        130             135                 140

His Ser Leu Val Ser Phe Val Val Arg Ile Val Pro Ser Pro Asp Trp
145             150                 155                 160

Phe Val Gly Ile Asp Ser Leu Asp Leu Cys Glu Gly Gly Arg Trp Lys
                165                 170                 175

Glu Gln Val Val Leu Asp Leu Tyr Pro His Asp Ala Gly Thr Asp Ser
            180                 185                 190

Gly Phe Thr Phe Ser Ser Pro Asn Phe Ala Thr Ile Pro Gln Asp Thr
            195                 200                 205

Val Thr Glu Ile Thr Ala Ser Ser Pro Ser His Pro Ala Asn Ser Phe
        210                 215                 220

Tyr Tyr Pro Arg Leu Lys Ser Leu Pro Pro Ile Ala Lys Val Thr Phe
225                 230                 235                 240

Val Arg Leu Arg Gln Ser Pro Arg Ala Phe Ala Pro Pro Ser Leu Asp
                245                 250                 255

Leu Ala Ser Arg Gly Asn Glu Ile Val Asp Ser Leu Ser Val Pro Glu
                260                 265                 270

Thr Pro Leu Asp Cys Glu Val Ser Leu Trp Ser Ser Trp Gly Leu Cys
            275                 280                 285

Gly Gly Pro Cys Gly Lys Leu Gly Ala Lys Ser Arg Thr Arg Tyr Val
        290                 295                 300

Arg Val Gln Pro Ala Asn Asn Gly Thr Pro Cys Pro Glu Leu Glu Glu
305                 310                 315                 320

Glu Ala Glu Cys Ala Pro Asp Asn Cys Val
                325                 330
```